United States Patent
Broker et al.

(10) Patent No.: US 6,605,281 B1
(45) Date of Patent: Aug. 12, 2003

(54) HUMAN PAPILLOMAVIRUS VECTORS FOR THE EPISOMAL TRANSDUCTION OF HOST CELLS AND METHOD OF MAKING SAME

(75) Inventors: Thomas R. Broker, Mountain Brook, AL (US); Louise T. Chow, Mountain Brook, AL (US); Eric J. Sorscher, Birmingham, AL (US); Nianxiang Zou, Homewood, AL (US); Vijayakrishna K. Gadi, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/530,047
(22) PCT Filed: Oct. 23, 1998
(86) PCT No.: PCT/US98/22476
§ 371 (c)(1), (2), (4) Date: Jul. 17, 2000
(87) PCT Pub. No.: WO99/20108
PCT Pub. Date: Apr. 29, 1999
(51) Int. Cl.$^7$ ............................ A61K 39/12; C12N 15/00
(52) U.S. Cl. ................. 424/199.1; 424/204.1; 435/320.1; 435/69.1; 435/235.1; 435/325; 435/252.3; 536/23.72; 536/23.1
(58) Field of Search .................... 424/199.1, 204.1; 435/320.1, 69.1, 235.1, 325, 252.3; 536/23.72, 23.1; 930/220

(56) References Cited

U.S. PATENT DOCUMENTS 5,674,703 A * 10/1997 Woo et al. .................. 435/69.1

FOREIGN PATENT DOCUMENTS

WO       WO 94/12629      *  6/1994

OTHER PUBLICATIONS

Gadi et al, American Journal of Respiratory Cell and Molecular Biology, May 1999; vol. 20 (5), pp. 1001–1006.*
Chiang et al, Journal of Virology, 1992, vol. 66 (9), pp. 5224–5231.*
Chiang et al , PNAS USA, vol. 89, pp. 5799–5803, Jul. 1992.*
Smith AE , The Lancet, 1999, vol. 354 suppl. 1, pp 1–4.*
NIH report , Orkin et al, 1995.*
Verma et al , Nature, 1997, vol. 389, pp 239–242.*

* cited by examiner

*Primary Examiner*—Ali R. Salimi
(74) *Attorney, Agent, or Firm*—Gifford, Krass, Groh, Sprinkle, Anderson & Citkowski, P.C.

(57) ABSTRACT

A replicon for delivery of a transgene for episomal gene expression in a mammalian host cell includes a transgene having an open reading frame or other nucleic acid sequence for transcription into RNA and under the transcriptional control of a first surrogate promoter and a first gene sequence expressing a papillomavirus replication initiator protein E1 tinder tile control of a second surrogate promoter. The replicon also includes second gene sequence expressing the papillomavirus replication origin binding protein E2 under the control of a third surrogate promoter, wherein tile transgene, the first and the second sequences are incorporated within at least one plasmid and less than three plasmids.

6 Claims, 11 Drawing Sheets

HUMAN PAPILLOMAVIRUS VECTORS FOR THE EPISOMAL TRANSDUCTION OF HOST CELLS AND METHOD OF MAKING SAME

GRANT REFERENCE

The subject invention was made with government support under a grant from the National Institutes of Health/National Cancer Institute, Grant No. CA36200 and a grant from the Cystic Fibrosis Foundation Research Development Program—Component 2, Grant No. R464. The government has certain rights in the invention.

FIELD OF THE INVENTION

The present invention relates to modified human papillomavirus vectors and to methods of making and using the same, as non-integrating episomal plasmids and to certain DNA sequences, inserted therein or expressed within a host cell of the viral vector. In particular, the invention relates to a papillomavirus, in particular human papillomavirus, in which a naturally occurring genome of the virus has been altered ("HPV vector"); to methods of making a vector and transducing cells therewith; to assure persistence of a vector, as an autonomous, extrachromosomal replicon maintained by the viral E1 and E2 replication proteins, despite the removal of all viral immortalization and transformation genes; and to certain DNA sequences inserted into or expressed in a host cell by way of an HPV vector, for purposes of long term gene transduction and expression for applications in genetic modification and therapy.

BACKGROUND OF THE INVENTION

Since the development of recombinant DNA technology some 25 years ago, the prospect of developing extrachromosomal gene expression vectors capable of long-term expression in transduced cells and/or tissues has become a reality with this invention. Prior developments in gene therapy research utilized vectors which either integrated the vector genome into the host chromosomes or were replication defective and non-persistent. The integration of the vector genome into a host chromosome is a potential and real cause of chromosomal insertional mutations and is vulnerable to unpredictable or uncontrollable inactivation of a reporter gene or a replacement gene. Retroviral vectors and adenovirus associated virus (AAV) vectors are representative examples of such insertional vectors. Alternatively, replication defective vectors may provide for cytoplasmic expression of vector genetic material within a host cell, but at the expense of the transduction behavior being lost over time in proliferating cells. Defective adenovirus and virus vectors are illustrative of vectors capable of transient expression in eukaryotic host cells, but with transduction being lost in proliferating cells. Other widely recognized deficiencies of certain viral vectors are their immunogenicity, and complications due to (a) prior immunity leading to immediate rejection of the infected cells and (b) induction of acute immune or hyperimmune responses within the first or second exposures during delivery of the vector to a host organism.

Thus, a novel vector capable of episomal replication transgene and regulated transcription can facilitate persistence and expression of a transgene in host cells without the limitations associated with insertional mutagenesis or disregulation or transgene expression disruption due to integration. These limitations have been observed in many in vivo studies using adenovirus or AAV vectors. J. M. Wilson, New Eng. J. Med. 1996, 334: 185–187. The human papillomaviruses have several attractive properties that are useful in augmenting gene expression and extrachromosomal maintenance in transfected cells.

The large family of papillomaviruses are significant human pathogens that infect epithelial tissues at selected body sites. Upon primary infection, or subsequent immunosuppression, papillomaviruses typically induce overt lesions variously called warts, papillomas or condylomata. These may go into short or long term remission. Nevertheless, viral DNA characteristically persists as episomes in stem cells. The episomal viral DNA may reactivate upon immunosuppression. A. Ferenczy et al., New Eng. J. Med. 1985; 313: 784–788, and A. Maran, Virology 1995; 212: 285–294. The latent phase of HPV infections is readily detected by Polymerase Chain Reaction (PCR) amplification of DNA. High levels of viral DNA amplification and mRNA transcription typically require terminal differentiation of squamous epithelia, and encapsidation into daughter viruses occurs in the superficial keratinocytes, prior to keratinocytes sloughing off the surface of the lesion. L. T. Chow and T. R. Broker, Viral Pathogenesis, N. Nathanson (Ed.), Lippincott-Raven, 1996, pp. 276–302. Well over 30 genotypes of human papillomavirus have an affinity for mucosal epithelia. E. M. de Villiers, Clinics in Dermatology 1997 (G. Orth and S. Jablonska, eds); 15: 199–206. Among the mucoscotrophic human papillomavirus strains are HPV-6, HPV-11, and HPV-16. While infections with HPV-16 occasionally progress to high-grade lesions and carcinomas, infections by HPV-6 or HPV-11 are almost universally benign and rarely reach such an advanced level of progression. In fact, most humans are infected with one or more types of cutaneous or mucosal HPV during their lifetime, and the virus persists thereafter under a degree of immunological surveillance and control, but without complete elimination. In almost all cases, such persistent maintenance remains subclinical with a small possibility of overt sporadic viral expression. For this and other reasons, HPVs are attractive vectors for long term gene therapy.

The HPV genome is a closed circular double-stranded DNA molecule, typically 7.9 kilo base pairs (kb) long. All HPV genotypes have a similar genome organization. The genomic organization of HPVs is known to the art and a representative prototype thereof, HPV-11, is set forth in FIG. 1. HPV genomes replicate as multi-copy nuclear, extrachromosomal plasmids. The differences in pathogenesis among various strains of papillomavirus mainly reside in the viral encoded E6 and E7 genes and in the upstream regulatory region (URR).

The lesions and possible carcinomas associated with papillomavirus infections are not associated with expression of HPV E1 and E2 replication proteins; rather the severe pathogenesis is initiated by inopportune expression of the viral oncogenes E6 and E7. The high risk oncogenic HPV-16, HPV-18 and related virus strains can cause disregulation in cell growth, cell differentiation and apoptosis. The natural functions of the oncoproteins are to reactivate the host DNA replication machinery in order to facilitate viral DNA amplification in differentiated keratinocytes that otherwise no longer express the host replication proteins. Consistent with these functions, HPV E6 and E7 genes are normally under the control of a differentiation-dependent upstream regulatory region (URR) promoter.

The E7 protein interacts with and inactivates the retinoblastoma susceptibility protein, pRB, a host tumor suppressor protein. M. Scheffner, et al. Curr. Top. Microbiol Immunology, 1994; 186: 83–99. This and/or related interactions reactivate the entire host DNA replication machinery in differentiated cells so that the virus DNA can amplify. Host DNA also replicates under these conditions as a by-product of the action of E7. S. Cheng, et al. *Genes Dev.* 1995; 9:2335–2349. The E6 protein inactivates another tumor suppressor protein, p53, thereby allegedly inhibiting premature apoptosis mediated by p53 when unscheduled DNA replication occurs in the differentiated cells in response to HPV E7 function. The cumulative result of HPV E6 and E7 protein activity in the differentiated stem cells can, in combination with presently unknown mutations in cellular genes, result in the immortalization of human keratinocytes in vitro or in host lesions. These proteins also are capable of transforming primary rodent epithelial cells in concert with an activated oncogene such as c-ras or c-fos. L. T. Chow and T. R. Broker, Ibid; and M Scheffner, et al., Ibid.

Downstream of the E2 gene in an HPV genome is the E5 gene, as shown in FIG. 1. HPV E5 protein is not an oncogene; however, it enhances the signal transduction of the EGF (epidermal growth factor) receptor, and can cause other membrane alterations. H. Stoppler, et al. *Intervirology* 1994; 37:168–179. Thus, HPV E5 protein augments the immortalization function of E6 and E7, yet E5 alone is not capable of immortalizing primary cells. M. C. Stoppler, et al., *Virology*, 1996; 223:251–254. While the role of HPV E5 is not fully appreciated in the literature, the bovine papillomavirus type 1 (BPV-1) E5 is the major viral oncogene. A key distinction from the HPVs, BPV-1 E5 functions to transform established rodent cell lines in vitro. BPV-1 E5 is detected in basal as well as in suprabasal differentiated cells of bovine warts caused by BPV-1. In light of the pathogenic nature of BPV E5 protein as well as other BPV proteins, such vectors raise a concern about the potential of E5-like proteins for oncogenesis. Previous attempts to design a viral vector suitable for episomal expression of foreign DNA in eukaryotes have met with only limited success due partly to the inability to separate deleterious viral genes from essential viral regulatory sequences. The instant invention largely overcomes these difficulties concerning vector design because the HPV oncoproteins are distinct from the HPV proteins necessary to support DNA replication from the native viral origin sequences. L. T. Chow and T. R. Broker, Ibid. The E6 and E7 viral oncogenes are normally up-regulated upon differentiation in HPV infected cells.

Similarly, HPV E4 protein function is not fully understood. E4 is known to associate directly or indirectly with cytokeratin intermediate filaments, but additional functions are postulated to exist. It is known, however, that HPV E4 is not an oncogene.

In contrast, to other members of the papovavirus family, such as mouse polyomavirus, simian virus 40, and human BK and JC viruses, for which the viral replication initiator and the oncogenic proteins are one and the same, HPV DNA replication utilizes host-encoded DNA replication enzymes, illustratively including DNA polymerases α and δ, PCNA, RF-C, RPA, DNA ligases and topoisomerases I and II. In addition, HPV replication utilizes host enzymes for the synthesis of deoxyribonucleoside triphosphate substrates. The virus contributes three components that are highly conserved among the papillomaviridae, which include: (1) the origin sequence (ori), (2) the ori recognition protein E2; and (3) the initiator protein E1. L. T. Chow and T. R. Broker, *Interviroloy* 1994, 37: 150–158; and A. Stenlund, *DNA Replication in Eukaryotic Cells* 1996: pp. 679–697.

The ori consists of binding sites (BS) for the two viral proteins E1 and E2 and is located within a noncoding, transcription regulatory region of approximately 750–1000 base pairs, designated the upstream (5') regulatory region (URR). The URR also contains numerous host transcription factor binding sites that are thought to confer tissue tropism. H. U. Bernard and D. *Apt, Arch. Dermatol.* 1994, 130:210–215. E2 protein binds tightly to the multiple E2BS in the URR and helps recruit E1 to the origin. In addition, upon binding to E2BS, E2 also functions as a transcription factor and activates a surrogate promoter at a distance, depending on its concentration and those of other, host transcription factors. Hirochika et al., *Genes Dev.* 1988, 2:54–67; McBride et al., *J. Biol. Chem.* 1991, 225:18411–18414; Ham et al., *Trends in Biochemical Sciences* 1991, 16:440444. In its capacity as a replication and transcription factor, E2 bound to E2BS prevents nucleosome formation around the origin and help recruit E1 and perhaps host proteins to the origin to establish an initiation complex. A complex of approximately 6 copies of E1 which dimerizes to form a double hexamer is a helicase and helps unwind the ori and recruit the host DNA polymerase a to initiate replication. The E1 complex is required continuously during the elongation phase of replication, unlike the transient requirement for E2 during assembly of the pre-initiation complex on the origin. Because of sequence and functional conservation, E1 and E2 proteins encoded by the same virus can promote the replication of either a homologous or a heterologous papillomaviral origin. C. M. Chiang et al., *Proc. Natl. Acad. Sci. USA* 1992, 89:5799–5803; A. Del Vecchio et al., *J. Virol.* 1992, 66:5949–5958; F. Sverdrup and S. A. Khan, *J. Virol.* 1994, 68:505–509. Furthermore, replication from an HPV origin is not restricted to human or epithelial cells as long as adequate levels of E1 and E2 proteins are produced/generated from expression vectors. C. M. Chiang et al., Ibid. This is the basis for transient replication in transfected culture cells. M. Ustav and A. Stenlund, *EMBO, J.* 1991, 10:449–457. From their biochemical properties, it is clear that the E1 and E2 viral replication proteins are not oncoproteins.

The current knowledge of the mechanisms of HPV pathogenesis and of origin-specific DNA replication are utilized in the instant invention to design HPV based vectors without the risk of introducing viral oncogenes into a host cell. Thus, the instant invention exploits the property of HPV that the viral replication components and viral oncogenes are separable. The most commonly used strategies for delivering potential therapeutic genes into cells are based on retroviruses, adenoviruses, adenovirus-associated (parvo) virus (AAV), and recombinant DNA plasmids. Each has its limitations. Moreover, expression from the retroviral LTR tends to be down-regulated. The use of cellular gene promoters may overcome the problem. For adenoviruses, the strong host immune reaction to the highly immunogenic capsid proteins may prevent repeated application. AAV is limited by its size to approximately 5 kb of inserted DNA, and it integrates into host chromosomes nonspecifically. Transfection of plasmid DNA into cells is relatively inefficient compared to virus infection. Considerable efforts have been devoted to improve the efficiency of DNA transfection. A. R. Thierry et al., *Proc. Natl. Acad. Sci. USA* 1996, 193:11454–11459; E. R. Lee et al., *Human Gene Therapy* 1996, 7:1701–1717; N. Oudrhiri et al., *Proc. Natl. Acad. Sci. USA* 1997, 94:1651–1656. But the effectiveness of plasmid DNA is additionally restricted by the short duration in transfected cells for lack of replication of the transfected DNA. Papillomaviruses have properties that circumvent many of these impediments.

The instant invention is based upon the modification of the naturally occurring papillomavirus genome to produce vectors by rearrangement of the natural genome, by the removal of DNA from the genome, and by the introduction into the naturally occurring HPV genome of foreign DNA. Foreign DNA is defined herein as DNA naturally occurring in an organism other than HPV, or of synthetic origin. The genetic information designed for expression from the vector is introduced into a host eukaryote via a trophic vector. A vector of the instant invention represents an innocuous eukaryotic cloning vector for the expression of foreign DNA. The proclivity of HPV to infect specific eukaryotic epithelial cell types, the ability to separate the replication mediating viral gene sequences from those sequences responsible for oncogenesis and cellular growth control, and the capability to regulate the expression of the viral replication genes and transgenes by using previously characterized host or viral enhancers and promoters form the basis of the instant invention.

There exists a need for a gene therapy method that overcomes the problems of low-level transgene expression and expression for only a limited duration. The present invention fulfills this long-standing need in the art.

SUMMARY OF THE INVENTION

Vectors and methods are provided for introducing genetic material into host mammalian cells. More particularly, vectors and methods are provided for transferring a transgene to mammalian epithelial cells by way of a vector derived from a papillomavirus, such that the transgene undergoes episomal maintenance and expression. The instant invention harnesses the selectivity of a papillomavirus for specific mammalian host cell types, but is not restricted to epithelial cells. The episomal replication characteristics of HPVs are utilized for episomal transgene expression. In preparing a vector of the instant invention, gene sequences of the HPV genome which are oncogenic which otherwise up-regulate cell growth and/or DNA replication are excised in the course of preparing the vector.

A vector of the instant invention functions to deliver a transgene for episomal gene expression in a host cell. A vector of the instant invention generically contains: a transgene having an open reading frame or other desired genetic sequence and under the control of a surrogate promoter, and gene sequences expressing the HPV or other papillomavirus viral replication initiator proteins E1 and E2, expression of these proteins being controlled by another surrogate promoter, wherein the transgene and viral replication protein gene sequences are either contained within a single plasmid or located on two separate plasmids, which are cotransfected as an operative vector. The expression of the transgene, E1 and E2 all benefit by the presence of HPV URR. For the purposes of modification to achieve transfection in diverse cell types, the expression of the E1 and E2 and transgenes is or can be regulated by other enhancer-promoter units.

Upon transfection, the vector of the instant invention persists as an autonomous replicon following cell division an/or differentiation. The transgene is selected to serve any number of utilities, illustratively including: correction of an autosomal or somatic genetic or metabolic deficiency; expression of a viral or prokaryotic protein or immunogenic fragment thereof, expression of a polypeptide foreign to the host; and modulation of: hyperproliferative diseases (such as cancers), apoptotic diseases, and states of infectious diseases of viral, bacterial, or protozoan origin for purposes of control, reversal, cure or vaccination.

DETAILED DESCRIPTION OF THE INVENTION

Figure 1:
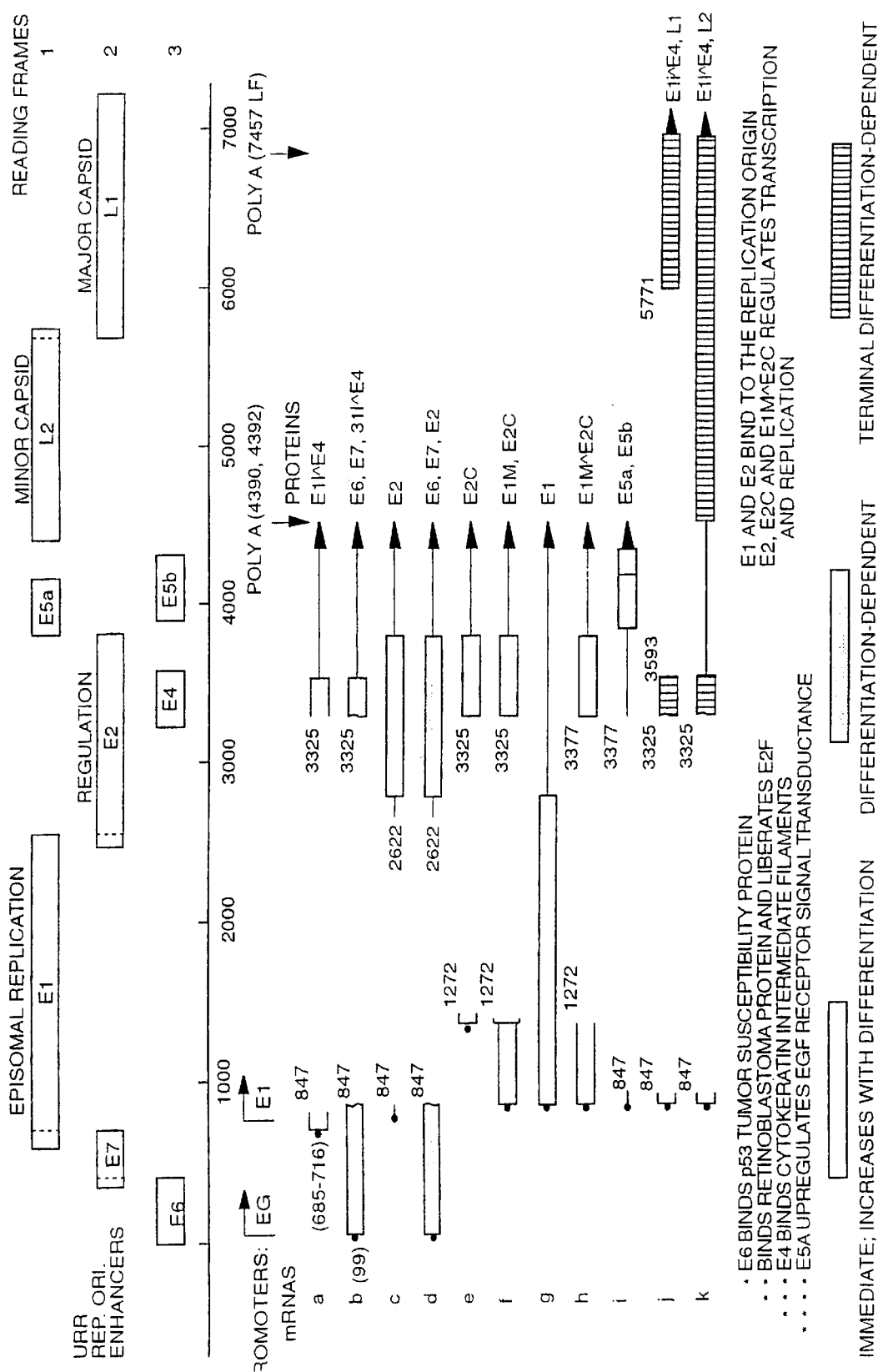
FIG. 1 is the prior art genomic organization of HPV-11, the most likely functions of proteins and sequences are labeled herein, and the virus is able to encode more proteins than it has open reading frames due to alternative utilization of promoters, poly A sites and mRNA splicing.
Figure 2:
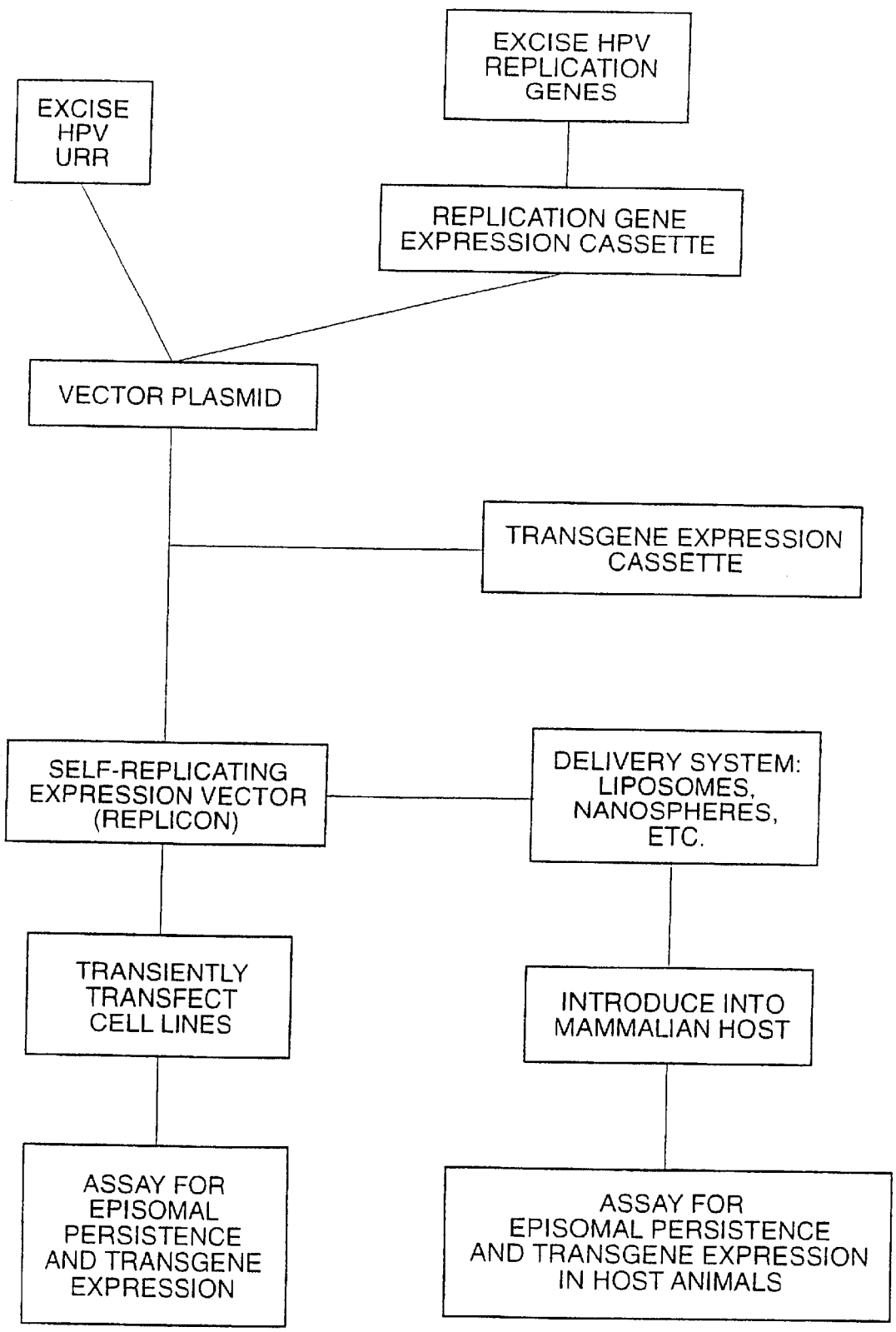
FIG. 2 is a schematic illustrating a production method of a one plasmid replicon of the instant invention and methods of using same to produce episomally transduced mammalian host cells.

Vectors and methods are provided for introducing genetic material into trophic host cells. More particularly, vectors and methods are provided for transferring a transgene to mammalian epithelial cells by way of a vector derived from a papillomavirus, such that the transgene undergoes episomal maintenance and expression. FIG. 2 is a schematic drawing illustrating the methods of the instant invention, including the production of a single plasmid vector (replicon) and the use of a vector of the instant invention to episomally transduce a mammalian host cell. The instant invention harnesses the selectivity of papillomavirus for specific mammalian host cell types but is not restricted to human epithelial cells. The episomal replication characteristics of papillomaviruses are utilized for episomal transgene expression. In preparing a vector of the instant invention, gene sequences of the papillomavirus genome which are oncogenic are excised.

As referred to herein, the term "transgene" or "reporter gene" relates to a nucleic acid, either naturally occurring or synthetic, which encodes a sense or an antisense transcript; a ribozyme; triplex or quadriplex-forming RNA; an RNA complementary to functional RNAs, including: RNA components of enzymes, including telomerases and nucleases; or a protein product. The term "nucleic acid" is intended to mean natural and/or synthetic linear, circular and sequential arrays of nucleotides, for example cDNA, genomic DNA (gDNA), mRNA, oligonucleotides, and derivatives thereof The phrase "operatively-linked" is intended to define attached in a manner which allows for transgene transcription. The term "encoding" is intended to mean that the subject nucleic acid is capable of transcription and translation into either the desired polypeptide or the subject protein or transcription into the desired RNA in an appropriate expression system, such as when the subject nucleic acid is linked to appropriate control sequences such as promoter and enhancer elements in a suitable vector and when the vector is introduced into an appropriate system or host cell. The term "polypeptide" refers to an amino acid sequence which comprises a full length protein and fragments thereof The elements of a replicon are previously provided, and generally the term "replicon" defines herein a eukaryotic gene expression vector system that remains extra-chromosomal upon introduction into an appropriate system or host cell, the replicon containing a portion of the HPV genome capable of persisting episomally in a cell, transducing the host cell with a transgene and replicating, but lacking in oncogenic sequences. Conversely, the autonomous replicon is optionally designed to express an "anti-sense" transcript for the purpose of hybridizing to a naturally produced RNA to inactivate it or, through enzyme activity, to target a host cell for destruction. Moreover, the HPV-based plasmid expression system may be designed to produce an RNA product that can establish a triplex or quadruplex with DNA present in the transduced cell.

The process of producing a single plasmid vector of the instant invention involves a series of steps. These steps include:

1. Incorporating the HPV URR fragment (origin and enhancer) and expression cassette to express only HPV E1 and E2 proteins from the viral genomic DNA fragment into a basic vector that contains a selectable marker.

2. Incorporating a transgene into a separate expression cassette in the same plasmid.

3. Transfecting the one-plasmid replicon into cell lines for testing plasmid persistence and transgene expression over time. Plasmid persistence is established by digestions with certain one cut or few-cut restriction enzymes plus Dpn I, using low molecular weight DNA recovered from lysed cells, followed by Southern blotting or by PCR amplification of the transgene.

4. Transfecting the one-plasmid replicon into immuno-compromized SCID mice or immune-competent mice for testing plasmid persistence and transgene expression over time. Plasmid persistence will be established by digestions with certain one-cut or few-cut restriction enzyme and by Dpn I, using low molecular weight DNA from lysed cells followed by PCR amplification of the transgene.

5. Depending on the outcome, the expression cassette for either E1 and E2, the transgene or both may be modified to modulate the expression to desired and efficacious levels.

Figure 3:
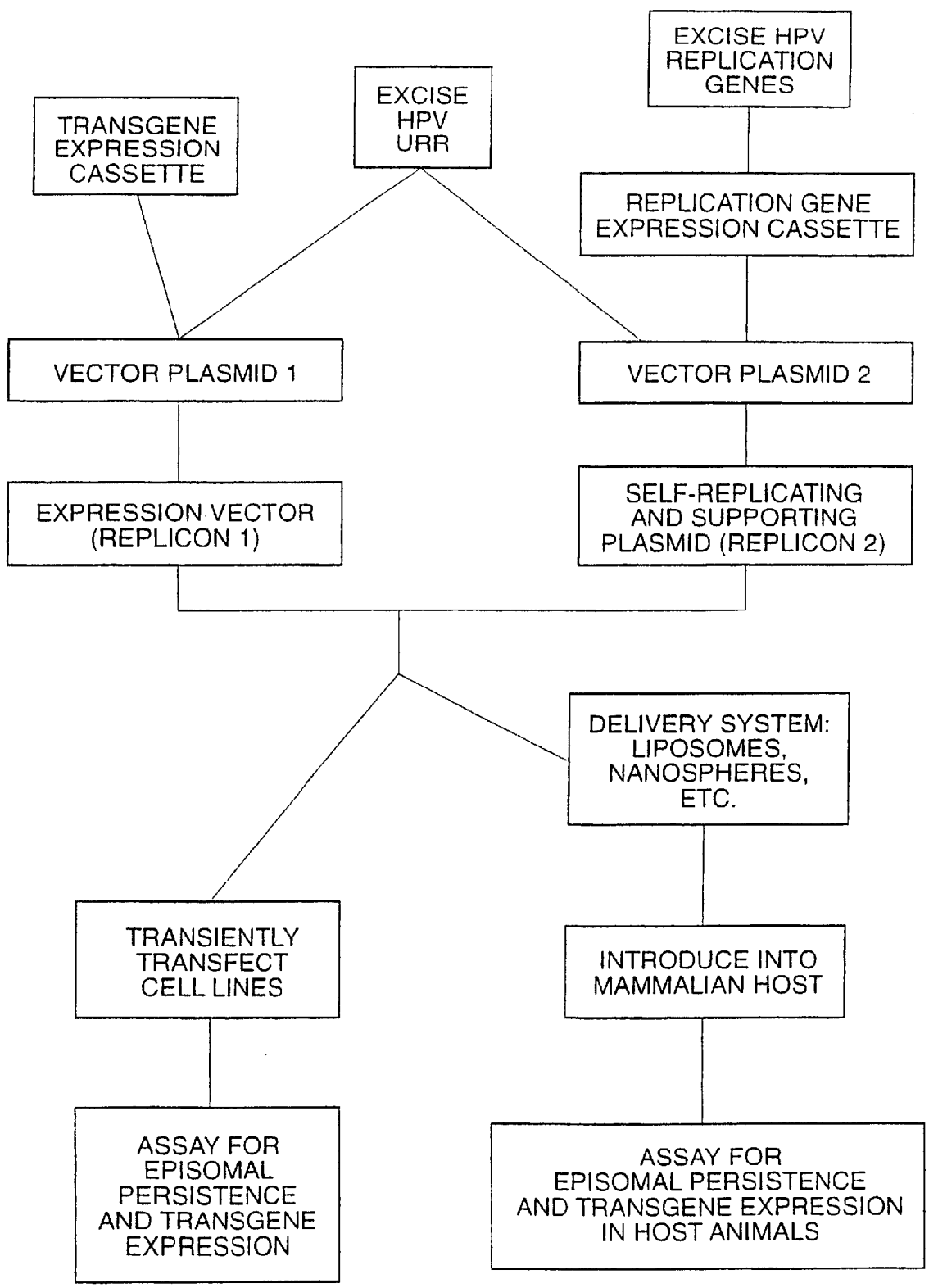
FIG. 3 is a schematic illustrating a production method of a two plasmid replicon of the instant invention and methods of using same to produce episomally transduced mammalian host cells.

FIG. 3, is a schematic illustrating a production method for a two plasmid replicon of the instant invention. The production method detailed in FIG. 3 varies from that for a single plasmid replicon in that:

the transgene is incorporated into a separate expression cassette in a plasmid other than the plasmid expressing E1 and E2 proteins; and this second plasmid contains the HPV replication origin and is therefore able to replicate in response to E1 and E2 protein binding; and the two plasmids expressing (E1/E2 or transgene) are cotransfected to effect episomal transgene expression.

It is appreciated that the components in the one- and two-plasmid replicons are completely modular, and different combinations are readily tailored to suit each specific application. The particular HPV URR is selected upon consideration of the target host cells. For the particular example of the treatment of cystic fibrosis in airways, the HPV-11 URR is incorporated both as an origin for replicon replication and also as an enhancer for transgene expression in airway cells. For expression in cells of the uterine cervix, tropism makes the HPV-16 URR or the HPV-18 URR preferable. The HPV-16 URR and HPV-18 URR each contains four E2 binding sites (E2BS) and one E1 binding site (E1BS) and each functions as an origin of replication in the presence of any matched pair of HPV E1 and E2 proteins, illustratively including HPV-16 E1 and E2 proteins; HPV-18 E1 and E2 proteins; or even the bovine papillomavirus E1 and E2 proteins. In some of the recombinant DNA constructions, a URR optionally also doubles as a promoter or optionally provides the polyadenylation signals and polyadenylation sites. The multiple use of a URR in the design of a replicon makes it possible to construct replicons smaller than otherwise would be possible. For these reasons, it is appreciated that the E1 and E2 protein pairs are derived from any of the human or animal papillomaviruses. In the representative examples of the instant invention in which both E1 and E2 proteins are expressed from the same plasmid, the E1 is tagged with the EE-epitope only for the convenience of cloning and assay. The URR plasmid is readily replicated using E1 protein without the EE epitope tag.

A transgene expression cassette of the instant invention contains an enhancer-promoter, the coding region of one or more proteins (or other desired elements to be transcribed into RNA), and a 3' polyadenylation (polyA) signal and polyA site. The enhancer-promoter for expressing the E1 and E2 proteins or the transgenes is varied so as to target a specific host cell or tissue types to the desired or efficacious levels.

In particular, since E1 and E2 proteins are needed in dividing cells but not in quiescent or differentiated cells, optionally an expression cassette is selected which contains a promoter of a host replication gene. For human hosts, these replication genes illustratively include: DNA polymerase α (Pearson et al., *Mol. Cell. Biol.* 1991, 11:2081–2095) or PCNA (Morris and Mathews, *J. Biol. Chem.* 1990, 265: 16116–16125). In particular, the DNA polymerase α gene is shut off in differentiated cells (Moore and Wang, *Cell Growth Diff.* 1994, 5:485–494). Thus, the usage of a host replication promoter prevents the synthesis of E1 and E2 proteins in non-proliferating cells and minimizes the host immune responses which could eliminate the transduced cells. The use of a promoter of host replication genes also ensures universality of its expression in proliferating human and animal cells regardless of cell types, because the signals that control proliferation are highly conserved in mammals and perhaps all the vertebrates.

The promoter for the transgene optionally also targets the desired cell or tissue types. Promoters of tissue- or cell-type specific genes (for instance, epithelial cells, liver cells, brain cells, cells of the immune system) are available, as are constitutive promoters for housekeeping host genes (such as the β-actin promoter) or viral promoters (such as the retroviral promoter from the Moloney Murine Leukemia virus, the Rous Sarcoma virus, the SV40 early promoter, the human cytomegalovirus immediate early promoter, and the adenovirus major late promoter, and the like), or differentiation-stage specific genes (such as high molecular weight keratins or filaggrin), or genes characteristically turned on or upregulated in disease states. Most of these promoters have no species barrier. Conditional promoters are also available commercially, such as the "tet on" which is turned on in response to tetracycline.

The vectors of the instant invention are hereby termed "autonomous replicons." A replicon of the instant invention has the following characteristics: (1) Expression of papillomavirus replication proteins E1 and E2; (2) an HPV origin of replication (ori) in functional linkage to the HPV gene sequences encoding E1 and E2, this DNA/fragment also contains a promoter element, and optionally enhancer elements, (3) a transgene under the control of a separate constitutive or regulatable promoter. It is appreciated that the papillomavirus genes and a transgene are located within a single plasmid, or alternatively a replicon of the instant invention involves multiple cooperating expression plasmids.

Figure 4:
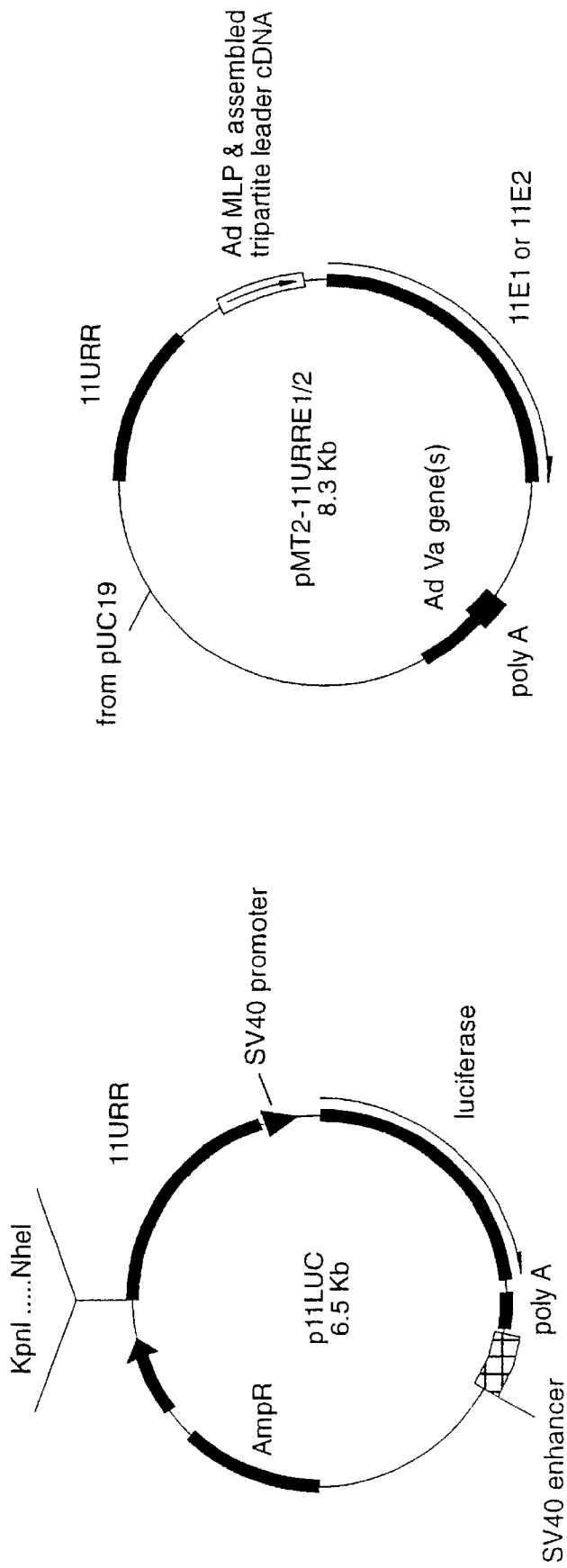
FIG. 4 is a schematic illustrating the construction of p11LUC, pMT2-11URRE1 and pMT2-11URRE2, where p11LUC is derived from pGL3c by inserting the 1 kb HPV-11URR into the parental plasmid. pMT2-11URRE1 and pMT2-11URRE2 are expression vectors for E1 and E2 proteins derived from pMT2-11E1 and pMT2-11E2, respectively by inserting the 1 kb HPV-11URR into the parental vector; AdMLP therein defines the adenovirus major late promoter.

A schematic of a proof of principle three plasmid replicon system of the instant invention is detailed in FIG. 4. It is appreciated that the 3 kb luciferase gene shown in FIG. 4 is an illustrative reporter gene and is readily replaced with any transgene or segment thereof. It is understood that it is well known to the art how one proceeds in excising a given transgene; cloning an alternative gene sequence DNA or other DNA elements illustratively including: anti-gene—antisense, a sequence that produces RNA products, a sequence that serves as a binding site sink for interactions with macromolecules or small molecules, and a sequence for the purpose of modulating nucleic acid metabolism; and adapting a given transgene for insertion into a plasmid of the instant invention using restriction enzymes. By way of illustration, a gene which codes for a protein defective in humans stricken with cystic fibrosis, the Cystic Fibrosis Transmembrane Regulator (CFTR) gene represents such a transgene. Upon replicon introduction into a suitable host cell, the host cell is transduced and expresses the transgene. For example, in a human suffering from cystic fibrosis (CF), the tropism of HPV for epithelial cells is exploited to transduce such cells of the respiratory tract so as to express the transduced CFTR gene which is deficient in CF sufferers. Other transgenes operative herein illustratively include: host cell genes that are otherwise lacking or defective, such as in autosomal genetic diseases; host cell genes that are otherwise lacking or defective that cause somatic deficiencies; enzyme encoding genes which are otherwise lacking or defective; structural protein genes which are otherwise lacking or defective; viral genes or immunogenic fragments thereof, so as to impart immune response to the viral gene sequence or translation products of the sequence; host cell or foreign antigen encoding gene sequences; genes coding for immune system-mediated clearance of malignant cells, such as histocompatibility antigens, cytokines or tumor growth factors; foreign genes for an enzyme capable of modifying a benign substrate to form a potent chemotherapeutic, such as Pseudomonas exotoxin A, diphtheria toxin, ricin; genes capable of processing prodrugs to drugs, such as herpes virus thymidine kinase or kinases that phosphorylate acyclic nucleoside phosphonates and *E.coli* purine nucleoside phosphorylase; and genes encoding for polypeptides having cell or systemic regulatory functions. Transgenes encoding for chromophoric or chromogenic products are also operative in the instant invention and find cosmetic applications, such as for tattoos.

A transgene, or fragment of a transgene, operative in the instant invention is produced and purified by any number of methods known to the art. A transgene is optionally produced synthetically or alternatively by treating mRNA derived from the transcription of a transgene with a reverse transcriptase so as to produce a cDNA version of the transgene, or a transgene is obtained by direct isolation from a gene bank, viral or plasmid transduction vector, or similar source.

A transgene of the instant invention is flanked by 5' control elements including an enhancer and a promoter, a translational control sequence and 3' elements illustratively including a polyadenylation signal and RNA stabilizing or destabilizing elements. In a three plasmid embodiment of the instant invention shown in FIG. 4, a luciferase reporter gene acts as a model transgene. The luciferase reporter is driven by a 5' flanking SV40 early promoter and enhancer. The reporter plasmid further includes an origin of replication, derived from a bacterial vector illustratively including the bacterial vector, pUC 19 and the entire HPV-11 URR, the URR containing several E2BS and one E1BS. A gene sequence coding for ampicillin resistance is optionally included in the transgene plasmid in order to amplify the plasmid during and after drug selection in E. coli. The other two plasmids making up a three plasmid replicon system of the instant invention are expression vectors for HPV E1 and E2 proteins, each of which also contains the HPV URR (ori). The HPV E1 and E2 proteins expressed are derived from the HPV-11 genome. Optionally, the E1 and E2 proteins expressed are derived from the HPV-16 genome or from other prototypes. It is appreciated that HPV-6 is biologically virtually indistinguishable from HPV-11 and illustrations of the instant invention utilizing HPV-11 are essentially synonymous with comparable constructions and strategies that are optionally utilized with HPV-6 and numerous other somewhat more distantly related HPV genotypes. The expression vector plasmids pMT2-11E1 and pMT2-11E2 support transient replication of the transgene/reporter gene contained within a separate plasmid or the same plasmid. Preferably, the 1 kb HPV-11 URR is inserted into the E1 and E2 expression plasmids, thereby yielding pMT2-11URRE11 and pMT2-11URRE2 of FIG. 4. The presence of the HPV-11 URR in the transgene plasmid increases luciferase expression by at least an order of magnitude as compared to pGL3c, the parental plasmid in which the luciferase reporter is expressed from the SV40 enhancer and early promoter. It is further preferred that the expression of the HPV E1 and E2 replication proteins is controlled by a single promoter. In this way, the expression of E1 and E2 proteins is coordinated and a preselected stoichiometry is maintained. More preferably, the transgene/reporter gene is controlled by an HPV URR, in addition to other enhancers and promoters, such as those of SV40.

Figure 5:
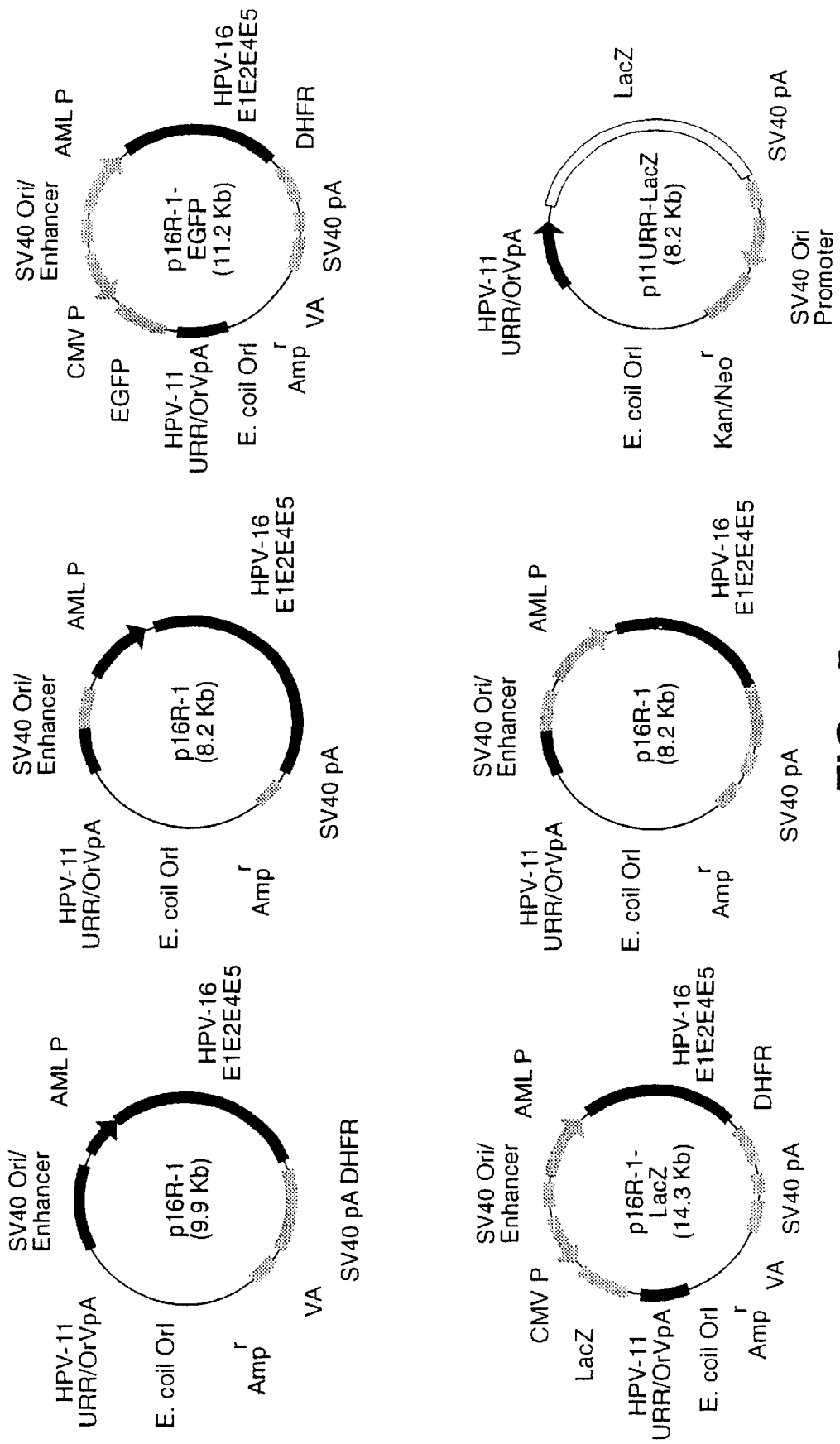
FIG. 5 is a schematic illustrating the construction of representative single plasmid replicons containing the HPV-11URR as an origin, wherein all p16R series replicons express HPV-16 E1 and E2 proteins from the same transcription unit. The p11-R1 replicon expresses epitope-tagged E1 and the native E2 proteins from the same transcriptional unit, the transgene herein is, for illustration, either the LacZ or the green fluorescence reporter protein.

Several versions of 2-plasmid and single-plasmid replicon systems are shown in FIG. 5. In the 2-plasmid embodiment of the instant invention, one plasmid expresses E1 and E2 proteins and also contains an HPV URR (ori), whereas the second plasmid expresses a transgene and also contains HPV URR (ori). In cells cotransfected by both plasmids, wherein both plasmids are replicated. In the one plasmid embodiment of the instant invention, all elements are incorporated into the same plasmid. The single plasmid replicon is the preferred embodiment of the instant invention owing in part to the efficiency of establishing a single plasmid in a host cell, as compared to multiple, complementing plasmids. The plasmids shown in FIG. 5 range in size from 7.8 kb to 14.3 kb, although plasmids of greater than 25 kb are operative in the instant invention. The features of the 2-plasmid and the single plasmid replicons of the instant invention are shown in FIG. 5 as follows: (1) Each plasmid expresses both E1 and E2 proteins from a single transcription unit, based on mapping data of HPV RNA isolated from condylomata. The E1 protein is thought to be translated from an unspliced message, whereas the E2 protein is translated from a spliced message which removes almost all the E1 coding region to about 100 nts upstream of the E2 open reading frame. L. T. Chow et al., J. Virol. 1987, 61:2581–2588, M. O. Rotenberg, Virology 1989, 172:489–497 and D. A. Palermo-Dilts et al., J. Virol. 1990, 65:3144–3149. In a single plasmid replicon, transcription of E1 and E2 is under the control of the same promoter, such as the adenovirus major late promoter, with the adenoviral tripartite untranslated RNA leader sequence at the 5' end operating to modulate translation efficiency. An adenovirus major late promoter has previously been utilized in expressing E1 and E2 from separate plasmids. C. M. Chiang et al., Ibid. It is appreciated that other tissue- and cell-cycle specific promoters are operative to drive E1 and E2 expression, illustratively including: Albumin promoter, PCNA promoter, and DNA pol α promoter. (2) One replicon expresses an epitope-tagged HPV-11 E1 protein known to function in transfected cells and in a cell-free replication system (S. R. Kuo et al., J. Biol. Chem. 1994, 269:24058–24065) and the native HPV-11 E2 proteins (p11R-1), whereas the remaining exemplary plasmids express the native HPV-16 E1 and E2 proteins (p16R series). There are several reasons for choosing HPV-16 replication proteins to replicate the HPV-11 origin. For unknown reasons, in the transient replication assay, HPV-16 E1 and E2 proteins replicated HPV-11 ori-containing plasmids more efficiently than the homologous HPV-11 E1 and E2 proteins. In carcinomas associated with HPVs, it is known that HPV-16 DNA is often found to exist as extrachromosomal plasmids, whereas the DNA of other virus types is often integrated into the host chromosomes, teaching that the HPV-16 functions may confer useful degrees of efficiency or selectivity. (3) All plasmids use the entire HPV-11 URR as origin and regulatory region. HPV-11 has a natural tropism for airway cells, most probably conferred by the enhancer elements in the URR. H. -U. Bernard and D. Apt, Ibid. Persistence of the plasmid appears dependent on the copy number of E2BS. M. Pariisoo et al., Ibid. The 1 kb URR has 4 E2BS versus 1 or 2 copies in a minimally operative origin of replication. Additional transcription factor binding sites in the URR also may be important for equitable plasmid segregation during cell division. (4) Some of the replicons shown in FIG. 5 also contain the bacterial lacZ gene or the green fluorescence protein (EGFP) reporter gene under the control of a cytomegalovirus (CMV) promoter. (5) To modulate the level of replication, the plasmids differ in either the presence or absence of the SV40 enhancer which affects expression of HPV replication genes and the Adenoviral VA (viral associated) RNA genes that influence mRNA translation efficiency.

For a given ori plasmid, the level of plasmid replication is related to the amounts of E1, provided a minimal amount of E2 is present. S-R Kuo et al., J. Biol. Chem. 1994, 269:24058–24065. The instant invention utilizes viral protein expression modulation as inferred from the extent of plasmid replication to promote long term plasmid maintenance with host cells.

Replicons having either HPV-11 or HPV-16 replication proteins demonstrate that individual expression vectors of HPV-16 E1 and E2 proteins replicated an HPV-11 or HPV-16 ori-containing plasmid more efficiently than did the wild type HPV-11 replication proteins expressed from the same expression vector. This difference has been attributed to a more efficient translation of mRNA with the 5' untranslated region of the HPV-16 E1 message. N. Zou et al., J. Virol. 1998, 72:3426–3441.

A surprising result of the instant invention involves the importance of reduced HPV E1 and E2 protein expression to promote long term maintenance of extra chromosomal plasmids. A technique for reducing HPV E1 and E2 protein expression includes deletion or disablement of the VA genes within a vector. Disablement of the VA genes inhibits excessive translation of mRNAs expressed from a promoter. The promoter illustratively including the adenovirus major late promoter (AMLP) as shown in p16R-2 of FIG. 5. The Ad VA RNA genes are known to influence translation efficiency from messages containing the 5' tripartite leader sequences. R. J. Kaufman et al. Mol. Cell Biol. 1985, 5:1750. The deletion or disablement operates to moderate replicon copy number, such that numerous cell doublings occur and the plasmid is maintained based on reporter gene activity. It is appreciated that other plasmids and promoters incorporated therein also exhibit overly-efficient mRNA translation, and gene disablement to limit mRNA expression is operative in such instances.

Another technique for promoting long term maintenance of extrachromosomal plasmids of the instant invention includes selection of HPV-11 E1 and E2 genes for expression since HPV-11 genes are expressed less efficiently than from other genotypes such as HPV-16. For instance, as the P11R-1 replicon of FIG. 5 expresses HPV-11 E1 protein tagged with a glutamate rich (EE) epitope and the native HPV-11 E2 protein. This EE-E1 has a reduced replication activity relative to the wild type E1 protein due to reduced protein level. Kuo et al., 1994. The persistence of replicons of the instant invention in rapidly dividing cell lines over nonreplicating plasmids shows that replicons like these are maintainable in transfected tissues in vivo, as cells do not divide as rapidly or the daughter cells become differentiated.

In one application, replicons of the instant invention deliver the transgene, human Cystic Fibrosis Transmembrane Regulator (CFTR), to human airway cells for expression. Because the significant morbidity and mortality associated with cystic fibrosis occurs in the lungs of cystic fibrosis (CF) sufferers, (as well as in other secretory tissues) there have been substantial efforts directed toward the development of pulmonary CFTR gene replacement therapy in the disease. Six clinical trials using a non-viral approach have concluded that the CFTR gene can be successfully transfected in human airways in vivo with cationic liposomes. E. J. Sorscher and M. J. Welch at the N. Amer. Cystic Fibrosis Mtg., *CF Human Gene Therapy Sym.* Orlando, Fla., 1996; E. J. Sorscher and M. J. Welch, Ibid; Caplen et al., *Nature Medicine* 1995, 1:39–46; J. Logan et al., *Gene Therapy* 1995, 2:38–49; S. C. Hyde et al., *Ped. Pulm. Suppl.* 1996, 13:264; D. R. Gill et al., *Gene Therapy* 1997, 4:199–209; and D. J. Porteous et al., 29ed *Pulm. Suppl.* 1996, 13:266. Comparatively low potency liposomal vectors, such as DC-Chol, DMRIE, and DOTAP, have each transferred CFTR to the nasal airways. In specific cases, evidence for bioelectric correction with these prior art vectors has been reported. These studies have shown that the nasal Potential Difference (PD) abnormality in cystic fibrosis patients is improved by a highly active plasmid containing strong promoters for CFTR expression when it is delivered as naked DNA or in complexes with liposomes. A liposomal formulation in such prior art studies was Lipid-67 (Genzyme Corporation, Framingham, Mass.), a reagent developed specifically for the purpose of lower airway gene transfer of CFTR. E. R. Lee et al., *Human Gene Therapy* 1996, 7:1701–1717. These initial results, following one-time administration in nasal airways in CF patients, have led to the development of more advanced studies of re-administration to the cystic fibrosis nasal mucosa or one-time dosing in the lower airways. The first lower airway administration study was performed at a dose of aerosolized material known to transfer reporter genes effectively to rodents and non-human primates. This human study showed bioelectric correction of the lower airway potential difference (PD) abnormality in several human subjects. E. Alton at the N. Amer. Cystic Fibrosis Mtg., *CF Human Gene Therapy Sym.* Orlando, Fla., 1996.

The levels of gene transfer required for bioelectric correction in cystic fibrosis airways makes the instant invention the most promising treatment modality for this disease symptom.

In situ hybridization and antibody localization studies have indicated that target cells for gene replacement in cystic fibrosis airways should include submucosal gland cells and the epithelial cells lining the large to medium sized airways. Indirect evidence from intestinal potential difference measurements in CF mice, from airway cells obtained via bronchoscopy of CF patients, and from model epithelial monolayers suggest that low levels of CFTR (e.g., 1 mRNA molecule/epithelial cell; 5–8% of cells in a monolayer; 5% of total CFTR in the murine intestine) are sufficient to overcome bioelectric defects in the disease. B. C. Trapnell et al., *Proc. Natl. Acad. Sci. USA* 1991, 88:6565–6569, J. F. Engelhardt et al., *Nature Genetics* 1992, 2:240–247; and J. R. Dorin et al., *Gene Therapy* 1996, 3:797–801. Pre-clinical studies in mice, rats, rabbits, pigs, and non-human primates and in vivo studies of CFTR gene transfer in humans with both viral and non-viral constructs have been limited by low levels of transgene expression. Although only a small number of cells expressing a small amount of CFTR mRNA might be sufficient for functional correction of CF chloride transport defects, (i.e. PD), other well described abnormalities in CF airways (for example, the elevated potential difference attributable to amiloride-sensitive sodium transport) require a much larger percentage of corrected cells in order to normalize these particular surrogate endpoints. L. G. Johnson et al, *Nature Genetics* 1992, 2:21–25. The development of means to further augment CFTR plasmid-based expression is an important issue based on the following considerations. 1) Not all patients treated with non-viral plasmid-type prior art vectors have demonstrated a bioelectric correction. 2) The level of improvement reported in prior studies among CF patients who exhibit improvement after lipid-mediated gene transfer has not indicated complete or permanent correction of chloride transport abnormalities. 3) Other CF defects that may contribute to disease pathogenesis require higher levels of CFTR transgene expression, either on a per-cell basis or from a standpoint of the percentage of cells corrected. L. G. Johnson et al, Ibid; and J. J. Smith et al., *Cell* 1996, 85:229–236. The instant invention describes the use of human papillomavirus (HPV) based replicons to augment plasmid-based expression of transgenes (by approximately two orders of magnitude or greater), in association with the possibility of plasmid persistence in airway cells.

Upon formation of a replicon, delivery of the replicon to a host cell is required. It is well known to the art that naked DNA or DNA "packaged" in different formats such as with lipid micelles or in conjugates with adenovirus and/or polylysine are suitable for gene delivery into host cells or animals for therapeutic development. There are several methods known to the art for delivery of the DNA contained within a replicon of the instant invention to host airway cells. Representative methods for replicon delivery to host cells in vivo include: uncomplexed "naked" DNA, and DNA complexed within a lipid, and DNA nanospheres. Each of these particular delivery methods is more fully elaborated upon below.

In general, the theories and applications discussed above and shown in the Examples below, are applicable to other papillomavirus types including those specific for vertebrate animals such as cows, dogs, sheep, horses, etc. Due to the similarities in papillomaviruses across their host range.

In order to demonstrate more fully the advantages arising from the present invention, the following examples are set forth by way of example only and are not intended as limitations of the claimed invention.

EXAMPLE 1

Up-regulation of Reporter Expression from a Replicon Containing the HPV-11 URR in a 3 Plasmid Replication System Transfection of HPV-11 E1 and E2 expression vectors pMT2-11E1 and pMT2-11E2 supports transient replication of a third plasmid which contains the URR from any of the HPVs when cotransfected into epithelial or fibroblast cells from different species. C. M. Chiang et al., Ibid. Thus, the collaboration among E1, E2 and the host replication proteins to initiate replication from a wide range of HPV origin sequences does not exhibit any species or tissue type specificity, providing that adequate quantities of E1 and E2 proteins are expressed. The entire HPV-11 URR containing four E2BS and 1 E1 BS (or subsets or duplications/multiplications thereof) is incorporated into a plasmid containing a luciferase reporter driven by the SV40 early promoter, pGL3c (Promega) to generate p11-LUC, as shown in FIG. 4A. Two days post-infection with p11 LUC, pMT2-11E1 and pMT2-11E2 into human kidney epithelial 293 cells, growing in vitro in a standard growth medium for this cell line, low molecular weight DNA is harvested. The low molecular weight DNA is indicative of replicated plasmid DNA. This is revealed by a Southern blot with a luciferase probe after Dpn I and Stu I digestion. The reporter plasmids replicated transiently as indicated by the Dpn I-resistant linear DNA after digestion with both Stu I and Dpn I. These results are demonstrated in the lanes marked by "+" in FIG. 6. Stu I linearized the p-11LUC plasmid, (AGG/CCT, in the vector) while Dpn I, which recognizes a four-base pair sequence, (GA/TC) cuts transfected DNA into small pieces at sites that are methylated when the DNA is isolated from bacteria. However, plasmid DNA which has replicated in eukaryotic cells is unmethylated at the Dpn I sites and is therefore resistant to Dpn I digestion. Human epithelial cell line 293 is cotransfected by the three plasmid replicon of the instant invention by standard electroporation techniques.

Figure 6:
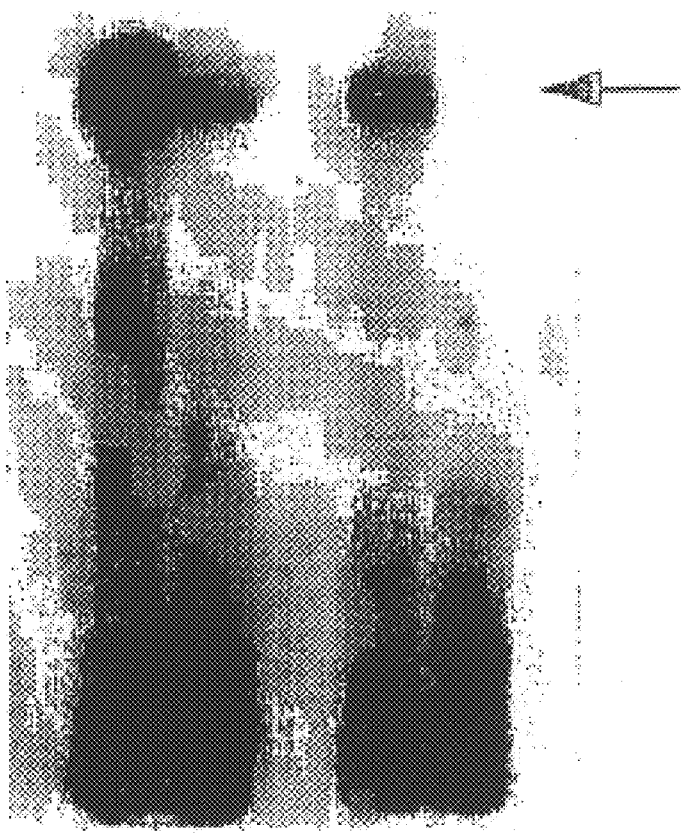
FIG. 6 is a transient replication assay of p11LUC in human 293 cells wherein p11LUC is electroporated into human 293 cells with pMT2-11E2 alone, or with both pMT2-11E1 and pMT2-11E2. Low molecular weight DNA is harvested two days post-transfection and digested with the DNA replication enzyme Stu I (−) to linearize p11LUC or with Stu I and Dpn I (+), where Dpn I degrades input DNA to yield clearly demonstrable unit length newly replicated DNA. The arrow herein points to linearized p11LUC.

In contrast, when pMT-2-11E1 or pMT-211E2 plasmid is omitted, the linear DNA is only detected when the low molecular weight DNA is digested with Stu I alone, as shown in the figures marked "−" in FIG. 6. In summary, FIG. 6 shows that Dpn I-resistant, linearized p-11LUC is only detected when all three plasmids are cotransfected (left 2 lanes of FIG. 6), but not when the E1 expression plasmid was omitted (right 2 lanes of FIG. 6).

Figure 7:
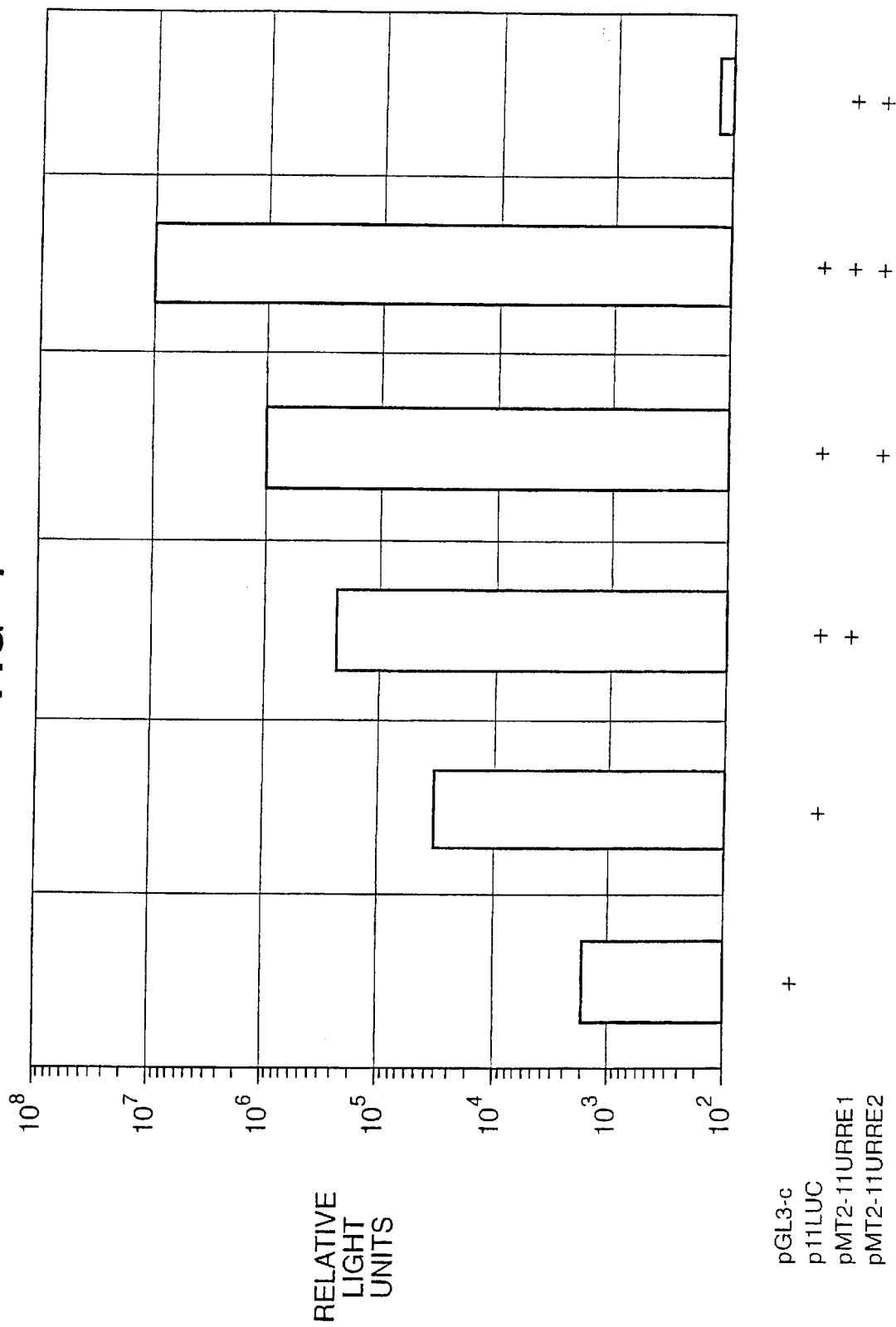
FIG. 7 is a histogram illustrating luminescence augmentation of the luciferase expression by HPV-11 cis elements and trans factors in human IB3-1 cystic fibrosis epithelial CF cell line. IB3-1 cells are transfected with various plasmids (indicated by +) mediated by DOTAP:DOPE cationic liposomes. The activity from the parental clone pGL3c is used as a reference. Transfection with only E1 and E2 expression vectors free of reporter genes serves as a negative control. Four days post-transfection, luciferase activities from triplicate experiments are determined and plotted on a log scale. Bars indicate standard error.

To further optimize this replicon system, the 1 kb HPV-11 URR is introduced as a controlling element into the E1 and E2 expression vectors, pMT2-11URRE1 and pMT2-11URRE2, respectively. FIG. 4B shows the structure of these plasmids. When transfected into a CF cell line, IB3-1, as mediated by cationic lipids, (DOTA: DOPE), p11-LUC had increased reporter activity relative to the parental clone, indicating that the URR functioned as a transcription enhancer in the airway cells as expected, based on HPV-11 tropism. The extent of the increased activity is shown in FIG. 7. Cotransfection with E2 further augmented luciferase expression (FIG. 7), consistent with an interpretation that the URR also acted as an E2-responsive enhancer in the presence of E2 protein. H. Hirochika et al., Ibid. When the reporter plasmid is cotransfected with the E1 expression plasmid, there is a comparable increase in luciferase activity above that of the reporter plasmid itself (FIG. 7). When the reporter was cotransfected with both E1 and E2 expression plasmids, an increase in reporter expression by nearly four orders of magnitude was obtained in CF airway cells, indicating that replication took place in the transfected cells. Low levels of transgene expression is one of the features generally acknowledged to limit liposome-mediated gene transfer in vitro and in vivo. The HPV-based replicons of the instant invention significantly augment plasmid transcription in CF airway cells and plasmid replication in vitro.

EXAMPLE 2

-Plasmid Replication in IB3-1 Cells

Southern blot hybridization detects extra-chromosomal replication only if a minimum of 15% of the cells are transfected. M. Ustav and A. Stenlund, Ibid. Over 40% of 293 cells are transfected by electroporation, making the replication assay by using Dpn I/Southern blot hybridization feasible, as shown in FIG. 6. In contrast, less than 5% of IB3-1 cells are transfected by lipid-mediated replicon transfer. This level of transfection is below the routine current limits of detection for the Dpn I-resistant, newly replicated DNA by Southern blot assay. In response, a PCR-based method is developed to investigate plasmid replication of a three plasmid replicon embodiment of the instant invention in vitro and in vivo. PCR amplification (without Dpn I digestion) has previously been used to demonstrate the presence of transfected plasmid DNA in mouse tissues after injection with DNA-liposomes. A. R. Thierry et al., *Proc. Natl. Acad Sci. USA* 1995, 92:9742–9746. IB3-1 cells are transfected with various combinations of reporter plasmid, p11-LUC, pMT2-11URRE1 and pMT2-11URRE2, using DOTAP:DOPE cationic liposomes. Low molecular weight DNA was harvested four days post-transfection and digested with either Stu I or with Stu I and Dpn I. PCR amplification with primers targeted to a 1.6 kb region of the luciferase gene is performed as described in Example 7. When the DNA is not digested with Dpn I, as shown in the left panel of FIG. 4A, a 1.6 kb PCR product is detected in all transfections, except when a luciferase reporter plasmid is omitted. When DNA is digested with Dpn I, a 1.6 kb band is only visible in cotransfection of p11-LUC and E1 and E2 expression vectors, but not after transfection with pGL3c alone, or p11-LUC alone, nor with E1 and E2 expression vectors in the absence of p11-LUC, as shown in the right panel of FIG. 4A. These results show that p11-LUC replicated in at least a fraction of the transfected cells in the presence of E1 and E2 expression vectors.

EXAMPLE 3

Three Plasmid Replication System in Mammalian Airways

Surface airway epithelial cells and alveolar epithelial cells are a predominant site of transfection with cationic lipids, but not all epithelial cells are transfected efficiently. Transfected surface epithelial cells represent only a fraction of the overall tissue in a total lung extract. Because of the relatively low efficiency of liposome mediated transfection in a mammalian airway, such as that of a mouse, it is not possible to perform transient replication assays using the Dpn I/Southern blot hybridization methods, as shown in FIG. 6.

Figure 8:
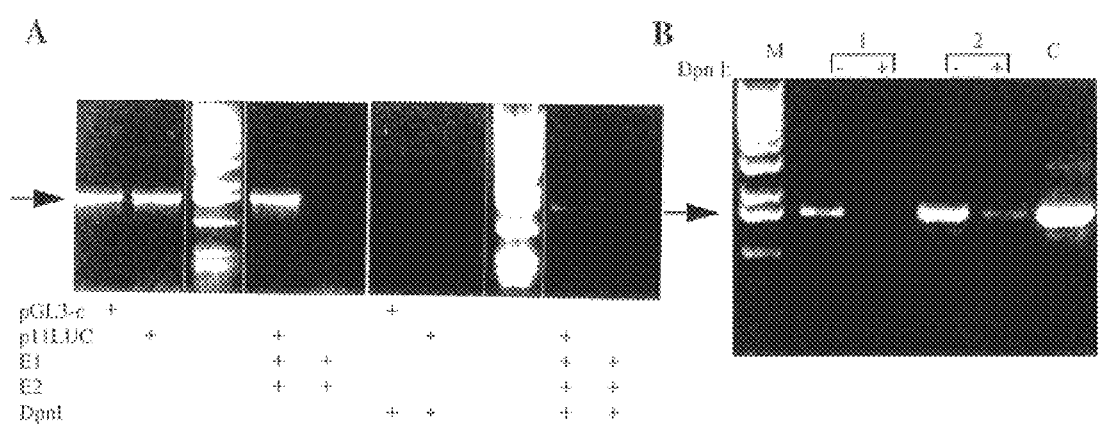
FIG. 8 is a transient replication assay of p11LUC in: (A) IB3- 1 cells four days post-transfection by plasmids and (B) in airways of FVB/N-C57BL/6 mice three days post-transfection, wherein low molecular weight DNA is digested with Stu I alone (−), or with Stu I and Dpn I (+). The digestion products were then amplified by using the polymerase chain amplification reaction with primers targeted to the luciferase reporter gene. Only replicated plasmids can generate the 1.6 kb PCR product. The arrows in (A) and (B) point to the 1.6 kb product from PCR amplification.

In response, the modified polymerase chain reaction (PCR) based test just described is used to test for plasmid replication in mouse airway tissues. The low molecular weight DNA from total mouse airway tissue is extracted three days post-transfection with the plasmids, as described in Example 2 in complex with GL-67 (Genzyme Corporation). After Stu I/Dpn I digestions, PCR amplification generated a 1.6 kb fragment only when all three plasmids of the replicon detailed in Example 2 are cotransfected, as shown in FIG. 8B, lanes 2. A 1.6 kb fragment is not generated when pGL3c is transfected alone, as shown in FIG. 8B, lane 1. This demonstrates successful transduction into some dividing cells and plasmid DNA replication in the same cells. A PCR based test not utilizing Dpn I digestion previously demonstrated persistence but not replication of transfected DNA in mice, as reported by Thierry et al., Ibid.

EXAMPLE 4

Three Plasmid Replicon Construction

The HPV-11 E1 and E2 expression vectors pMT2-1 E1 and pMT2-11E2 have been constructed previously. The construction and description of pMT2-11E1 and pMT2-11E2 is provided in C. M. Chiang, et al. Ibid pMT2-11URRE1 and pMT2-11URRE2 are constructed by inserting the 1 kb HPV-11 URR into the Stu I site in the SV40 enhancer. The 1 kb HPV-11 URR spans nucleotides 7072-7933/1-99 and is removed from clone 23-3 by Hind III digestion. The map of clone 23-3 is described in H. Hirochika, et al, ibid. 1988; 2:54–67; p11LUC is prepared by cloning the HPV-11URR fragment into pGEM-1 (Promega Corp.), excised by Bam HI-Nhe I double digestion, followed by insertion into the Bgl II/NheI sites in pGL3c (Promega Corporation), as per conventional techniques. pGL3c expresses the luciferase reporter from the SV40 early promoter. The structures of these plasmids of the instant invention are shown in FIG. 4.

EXAMPLE 5

Gene Transfer into Cell Lines 0.5 µg of the reporter plasmid together with: 1) 5 µg each of pMT2-11URRE1 and pMT2-11URRE2 or 2) 5 µg of pMT2-11URRE2 and 5 µg of unrelated filler plasmid DNA (a control) are electroporated into 5×10$^6$ human 293 cells, as described in Chiang, Ibid. One-third of the cells are plated onto a 100 mm Petri plate cultured in DMEM plus 10% fetal bovine serum (FBS) for 48 hr before harvesting the low molecular weight DNA. IB3-1 cells, airway cells derived from a CF patient (a gift of Dr. Pam Zeitlin, The Johns Hopkins University), are grown in 48 well plates in LHC-8 media (Biofluids, Inc.). The wells are transfected in triplicate with various combinations of pGL3c, p11LUC, pMT2-11URRE1, pMT2-11URRE2, and filler plasmid in a complex with DOTAP:DOPE cationic liposomes (Avanti) in a 4:1 lipid to DNA molar ratio as follows: a) 150 ng of p11LUC and 600 ng each of E1 and E2 expression vectors, b) 150 ng of p11LUC and 1,200 ng of filler DNA, c) 150 ng of p11LUC with 600 ng each of E1 or E2 expression vector and filler DNA, d) 150 ng of pGL3c and filler DNA, or e) 150 ng of filler DNA and 600 ng each of the E1 and E2 expression vectors.

EXAMPLE 6

Gene Transfer into Murine Cells

For in vivo gene transfer into FVB/N-C57BL/6 mice, lipid GL-67 (Genzyme Corp.) is complexed with the transgene DNA of interest. Preferably, the molar ratio of lipid to plasmid DNA for this purpose is 1:6. 108 µg of GL-67 are mixed with 250 µg of p11LUC and 200 µg each of pMT2-11E1 and pMT2-11E2 in a carrier volume of 550 µl. In the control experiment, 250 µg of pGL3 are mixed with 400 µg filler DNA. After a 15 minute incubation at 30° C., 100 µl of the lipid:DNA mixture are pipetted on the tip of the nares of lightly anesthetized mice over the duration of one minute. Three animals are treated with each lipid:DNA formulation. Three days later, mice are sacrificed by CO$_2$ poisoning and their lungs and tracheas removed. The tissues are processed as described in A. R. Thierry, Ibid. Ten to thirty mg of the tissues are extracted for low molecular weight DNA for replication assays.

EXAMPLE 7

Plasmid PCR Replication Assays in Vitro

Transient replication assays in human 293 cells are conducted as described in Chiang, et al. Ibid Human epithelial 293 cells are selected for replication and persistence because of the efficiency of transfection in these cells. 2 days post-transfection, low molecular weight DNA is harvested by the alkaline Hirt lysis procedure. Half the DNA from a 100 mm plate is digested with Stu I which linearizes the reporter plasmid, while the other half is cut with both Stu I and Dpn I. The Dpn I/Southern blot is used to demonstrate replication unequivocally. The digestion products are separated on a 0.8% agarose gel, Southern blotted onto a nylon membrane and then probed with the luciferase cDNA, which is $^{32}$P-labeled by random priming. An autoradiogram is developed after an overnight exposure.

PCR-based assays are used to detect plasmid replication in IB3-1 cells and in mouse airway tissues. Low molecular weight DNA is harvested 4 and 3 days post-transfection, respectively, and digested with restriction enzyme or enzymes as just described. Thirty cycles of PCR amplification are then conducted using primers 5'-TAAAAAGCTTATGGAAGACGCCAAAAACATAA AGAAA and 5'-GCCCAAGCTTATCGATTACACGGCGATCTTTCC GCCCTTCTT that target a 1.6 kb region of the luciferase gene. Each cycle consists of 30 sec at 95° C. for denaturation, 30 sec at 60° C. for annealing, and 90 sec at 72° C. for polymerization. The products are then run in a 0.8% agarose gel and revealed by ethidium bromide staining. A 1.6 kb PCR product amplified from the pGL3c plasmid is used as a positive control.

EXAMPLE 8

Luciferase Assay

Four days post-transfection of IB3-1 cells, cell lysates are harvested with 50 µl of luciferase assay buffer (Promega) and centrifuged to remove debris. The lysates are combined with luciferin reagent and read for light (bioluminescent) activity in a luminometer with signal integration for 10 sec., the results of which are indicated in FIG. 7.

EXAMPLE 9

One Plasmid and Two Plasmid Replicon Construction

The vectors that are used to construct the HPV single plasmid replicons are pMT2 and pMTX. The HPV-16 E1 and E2 protein expression vector pMT2 has been previously described. R. J. Kaufman et al., *Molecular and Cell Biol.* 1989, 9:946–958; and Kuo et al., Ibid. The HPV-11 URR (7072–7933/1-99) is inserted into pMT2 at the Stu I site located within the SV40 enhancer, as shown in FIG. 5. This fragment of the HPV-11 genome contains the polyadenylation signal for late viral genes, and the viral replication origin which overlaps the transcription regulatory region includes a promoter. Some representative single plasmid replicons of the instant invention are shown in FIG. 5, the construction of which follows: To assemble p16R-1, the HPV-16 genomic DNA fragment from nucleotides 686 to 4470 flanked by (Pvu I1 and Stu I) restriction sites, which includes the open reading frames (ORFs) of E1, E2, E4 and E5 as well as the polyadenylation site for early genes, is cloned into the pMT2 vector at the Pst I and EcoR I sites. To prepare p16R-2, the VA genes and the DHFR gene fragments are removed from p16R-1 by ligating the pMT2 fragment that spans the HPV-11 URR, SV40 ori/enhancer, adenovirus major late promoter, and HPV-16 genomic fragment containing between nucleotides 686 and 4470 into pUC19. To construct p16R-1-EGFP, a three-piece ligation was performed to piece together the Sal I-Spe I vector fragment from p16R-1; the blunted ended Sal I-Ase I fragment containing the CVM promoter and EGFP sequences from plasmid pEGFP-Cl (Clontech), and the Stu I-Spe I fragment which contains the SV40 ori/enhancer, Adeno ML promoter, and HPV-16 nucleotides 686–1462 (Spe HI) from p16R-1. In this construction the transcription of green fluorescence protein reporter (EGFP) gene uses the HPV-11 late polyadenylation site within the URR fragment. The EGFP gene is replaced by the LacZ gene to construct p16R-1-Lac Z. The plasmid p11R-1 contains the contiguous HPV-11 E1 and E2 ORFs from the genomic DNA (nts 832-3844), except that the amino terminus of E1 is tagged with the glutamic acid-rich (EE) epitope from the polyomavirus middle T antigen. T. Grussenmeyer et al. *Proc. Natl. Acad. Sci. USA.*, 1985, 82:7952–7954. To prepare p11R-1, the HPV-11 genomic DNA fragment (between nts 1380 and 3844) is amplified by the polymerase chain reaction (PCR), cut with SphI and is ligated to the 5' end of the EE-E1 coding sequences on pMTX-11EE-E1 SphI site (nt 1399) in the E1 ORF and EcoRI in the multiple cloning site of pMTX. pMTX is a derivative of pMT2 in which the multiple cloning site from pUC 19 was inserted into pMT12. S. R. Kuo et al., Ibid, 1994. p11URR-LacZ contains the bacterial neomycin-resistance gene excised from pLJd by digestions with SalI and ClaI. S. Cheng et al. (1995). In this clone, the HPV-11 URR serves multiple roles as the eukaryotic replication origin, the promoter of the LacZ gene as well as the polyadenylation site for the neomycin-resistance gene. The purification of all the plasmids is performed by two rounds of banding in CsCl-ethidium bromide equilibrium density gradient centrifugation.

In reducing the number of plasmids necessary to form a self-sustaining replicon set, the efficiency of plasmid persistence is increased, relative to a multiple-plasmid replicon set. Some of the representative plasmids shown in FIG. 5 contain a reporter gene such as the bacterial LacZ gene, or EGFP, controlled by the CMV promoter. Some of the representative replicons shown in FIG. 5 lack a reporter/transgene and are also useful in optimizing the levels of E1 and E2 proteins, as reflected by replicon copy number in transfected cells that an immune competent host tolerates.

EXAMPLE 10

Transient Replicon Replication Assays

Human kidney epithelial cell line 293 and human cervical carcinoma cell line C33 A are maintained in DMEM plus 10% calf serum in 5% $CO_2$ at 37° C. Transfections are conducted by electroporation, as described previously. C. M. Chiang et al., *J. Virol.* 1992, 66:5224–5231. At different times post-transfection, low molecular weight DNA is harvested by the alkaline Hirt method and treated with RNase. M. Ustav and A. Stenlund, Ibid Half of the low molecular weight DNA from one 100-mm plate is digested with Hind III, which cuts each plasmid two or three times. The other half is digested with both Hind III and Dpn I, which cleaves the input DNA that did not replicate into smaller fragments.

As indicated above, the newly replicated DNA is resistant to Dpn I digestion when these sites become unmethylated upon replication. The digestion products are separated in 0.8% agarose gels by electrophoresis. The gels are Southern blotted onto a nylon membrane. The DNA is detected by hybridization with $^{32}P$-labeled probes as specified for each experiment and exposed to X-ray films or PhosphorImager plates. The probes are labeled by the random priming method (Amersham).

Each of the six single- or two-plasmid replicons shown in FIG. 5 is capable of self-replication. p16-R-1 has the highest replication efficiency and produced the highest copy number of the replicons. p11-R-1 replicates to a more moderate extent, as shown in FIG. 4A. Generally, larger replicons with a reporter gene/transgene replicate to lower copy numbers than similar replicons, as shown in FIG. 8B. Replicons which lack either the SV40 enhancer or the VA genes replicate to a much lower copy number, as compared to those replicons containing such sequences (not shown). The low copy number associated with replicons lacking either the SV40 enhancer or the VA gene is attributable to the reduced transcription or translation of the E1 and E2 RNAs.

EXAMPLE 11

Persistence of HPV-16 R-1 and Reporter Gene Expression in Transfected Cells

Figure 9:
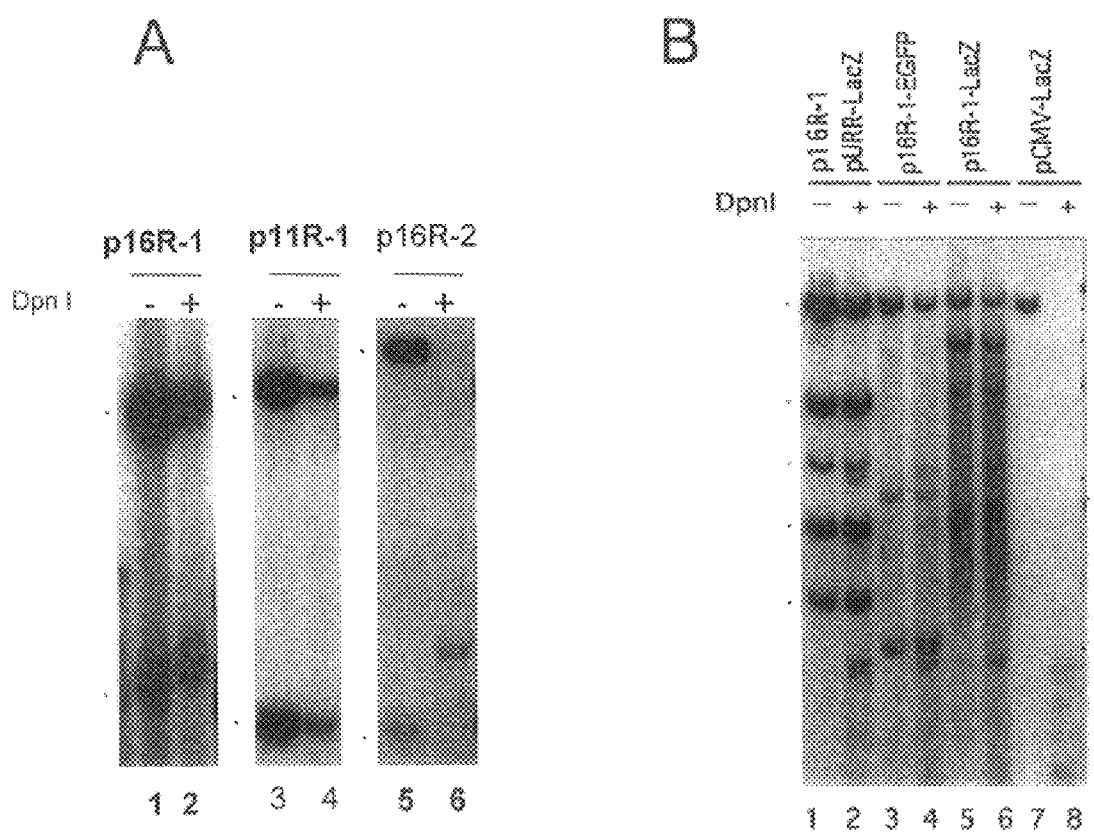
FIG. 9 is a transient replication assay in 293 cells of single plasmid replicons (panel A, lanes 1-6, panel B, lanes 3-6) or negative control (panel B, lanes 7, 8). The single plasmid replicon also supported the replication of a second reporter plasmid which contained an HPV URR, demonstrating the two plasmid system (panel B, lines 1,2). The cells transfected with plasmid (S) are as indicated, wherein two days post-transfection, assays are performed after digestion with the DNA restriction enzyme Hind III alone (−) or with Hind III (+) plus Dpn I (+). The probe for panel A is prepared by random priming of a pUC plasmid containing a portion of the HPV-11URR, whereas the probe used for panel B consisted of p16R-1 plus p11URR-LacZ; herein a dot signifies Hind III restriction fragments from replicated DNA.
Figure 10:
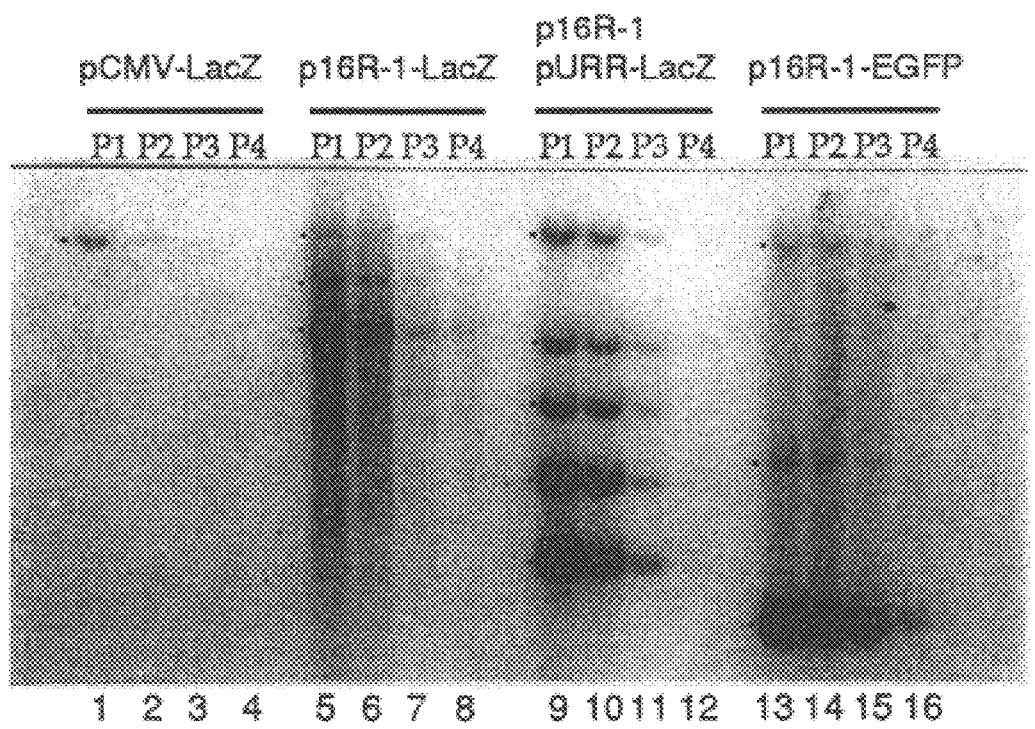
FIG. 10 is a persistence assay of 1 plasmid replicons during passage in transfected 293 cells, after electroporation with plasmid (s), cells are plated at 30% confluence on 100-mm plates and are passaged by splitting on days two, four, six, eight (P1, P2, P3, P4). Low molecular weight DNA is harvested on day four, six, eight and ten, digested with Hind III, Southern-blotted and probed; herein a dot symbolizes Hind III fragments from plasmid DNA remaining in the cells.
Figure 11:
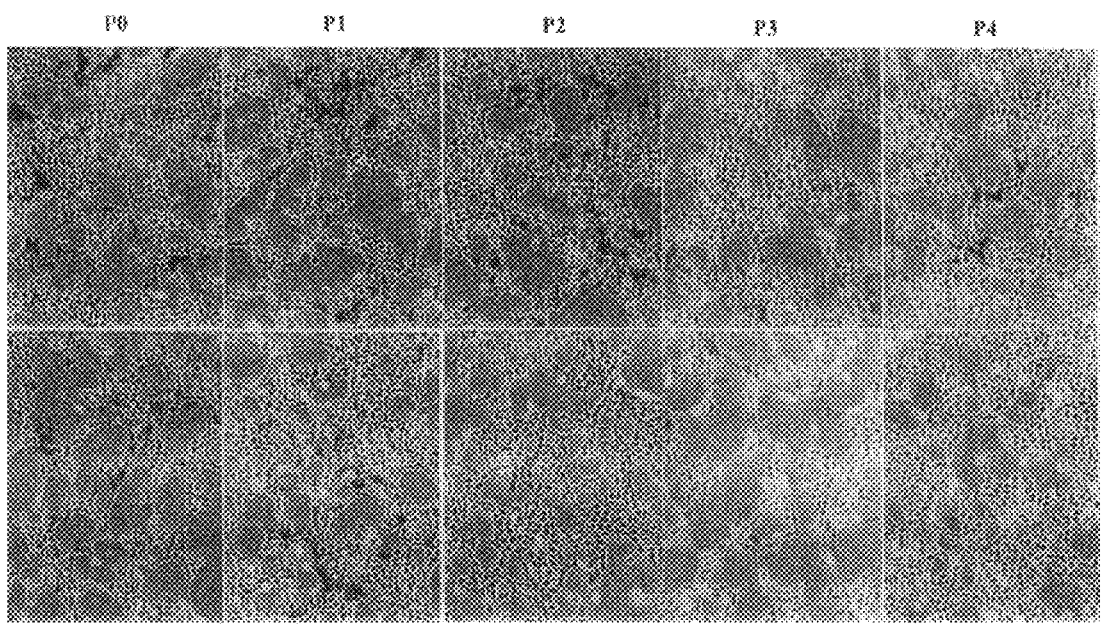
FIG. 11 is an assay of β-galactosidase activity in 293 cells during passage; cells are transfected with 1-plasmid replicon p16R-1-LacZ (top panels) or with negative control pCMV-LacZ (bottom panels) which does not replicate and then split 1:3 to 1:3.5 every two days over a period of ten days, and activities are assayed on days two, four, six, eight, and ten (labeled P0, P1, P2, P3, P4).

The 14.3 kb p16R-1-lacZ and 11.2 kb p16R-1-EGFR 1-plasmid replicons tested for persistence in the transfected and proliferating 293 cells over a 10-day duration are shown in FIG. 10. The cells are split at near-confluence approximately 1:3 to 1:3.5 every 2 days. Low molecular weight DNA is harvested from each passage, and Southern blotting is performed after Hind III digestion. Hind III cuts the various plasmids into several pieces. FIG. 10 shows the non-replicating pCMV-LacZ control plasmid is barely detectable after four days indicating that, in the absence of replication, most of the input DNA has been degraded by that time. In contrast, the p16-R-1 replicons are still detectable 10 days after being split 4 times in culture indicating plasmid persistence after approximately 8 to 10 cell divisions. In addition, with the helper plasmid present, LacZ-positive cells also persisted for 10 days whereas, in cultures transfected with pCMV-LacZ in the absence of the helper, only occasional LacZ-positive cells are detected on days 6, 8 and 10, as shown in FIG. 11.

p16-R-1 replicons persist through repeated cell divisions over the duration of the experiments, as shown in FIGS. 9 and 10.

EXAMPLE 12

Inhibition of E4 Protein Expression

The expression of E4 messenger RNA or protein may have a deleterious effect on the copy number tolerance of host cells. The replicons of the instant invention are optionally modified to limit the expression of the E4 mRNA or protein. The E4 splice acceptor site of the p16R-3 replicon of FIG. 4 has been site-mutated without changing the coding of the overlapping E2 open reading frame. The site mutation is carried out and screened for by standard PCR-mediated site-directed mutagenesis.

Alternatively, E4 protein synthesis is optionally prevented by introducing a premature stop codon into the E4 open reading frame by means of a conservative amino change in the overlapping E2 open reading frame. The amino acid change and subsequent screening for successful codon introduction utilizes conventional techniques known to the art, including PCR and restriction fragment swapping as just described. To minimize the size of the residual peptides translated, plasmids are selected in which the termination codon is introduced near the 5' amino terminal coding domain of the E4 open reading frame. When a termination codon is introduced into the E4 open reading frame with a conservative amino acid change in the overlapping E2 open reading frame in the hinge region of the E2 protein, the resulting replicon no longer expresses the E4 protein. Mutations eliminating E4 expression are confirmed by techniques including antibody detection of E4.

EXAMPLE 13

Alternative Promoter for E1 and E2 Genes

In the preceding examples, the E1 and E2 replication genes are under the control of the adenovirus major late promoter and contain the adenovirus tripartite leader in the 5' untranslated leader sequence. Alternative promoters include the HPV11 URR or, preferably, a promoter of a host replication gene, such as in the case of a human host being that for the DNA polymerase a (Pearson et al., *Mol. Cell. Biol.* 1991, 11:2081–2095) or PCNA (G. F. Morris and M. B. Mathews, *J. Biol. Chem.* 1990, 265: 16116–16125) is utilized, since E1 and E2 proteins are only needed to be made in dividing cells (where those host replication genes are normally expressed) but not in quiescent or differentiated cells. A host replication gene promotor is regulated during the cell cycle, for example, a DNA polymerase α gene is shut off in differentiated cells (A. L. Moore and T. S. Wang, *Cell Growth Diff.* 1994, 5:485–494). Thus, the usage of one such host promoter prevents the synthesis of E1 and E2 proteins in non-proliferating cells and minimizes host immune responses which might eliminate the transduced cells. The use of the promoter of the host replication genes also ensures universality of its expression in proliferating human and animal cells regardless of cell types, because the signals that control proliferation are highly conserved, in particular among mammals and generally among all vertebrates.

EXAMPLE 14

Removal of E5 Gene Sequences from HPV-16 Based Replicons

The E5 gene(s) is already removed from and lacking in the wholly HPV-11 origin replicons of the instant invention and can be removable from the HPV-16 replicons as well. The E5 genes are removed from the replicons of the instant invention, including those shown in FIG. 5, by PCR-mediated deletion from E4 negative mutant clones, as per conventional techniques.

EXAMPLE 15

An Alternative Promoter for a Reporter Gene/Transgene

In those instances where the reporter/transgene protein is responsible for eliciting an immune response in vivo, the expression of such a reporter/transgene protein is optionally down-regulated by a weaker promoter than that of SV40. An example of a weaker promoter is the HPV-11URR itself The HPV-11URR has low activity in undifferentiated keratinocytes and is up-regulated in differentiated epithelial cells of a mammalian host. Although HPV is trophic for epithelial cells, the HPV-11URR-driven reporter gene is present at only about 10% the level in mouse cell lines, as compared to human cells.

A transgene (or antisense sequence) is optionally expressed from a promoter of choice depending on the cell types to which the transgene is targeted. Promoters of tissue- or cell type-specific genes (for instance epithelial cells, liver cells, brain cells, cells of the immune system) are available, as are constitutive promoters for housekeeping host genes, such as the β-actin promoter or viral promoters illustratively such as the retroviral promoter from a Moloney Murine leukemia virus, a Rous Sarcoma virus, a SV40 early promoter, a cytomegalovirus immediate early promoter, an adenovirus major late promoter, and the like. Most of these representative promoters have no species barrier although their efficiency varies depending on the host. Conditional promoters are also operative herein and available commercially, such as the "tet on" which is turned on in response to tetracycline. For instance a transgene may be selected to be a suicide gene for cancer therapy, encode an enzyme which turns a harmless prodrug to a toxic drug, or that which causes apoptosis and thus should be under tight control until it is needed.

EXAMPLE 16

Reporter Genes

LacZ. This gene is attractive as a reporter gene because it confers the ability to identify transduced cells in tissue sections, which are visualized using X-gal or Bluo-gal (BRL/GIBCO) blue staining within specimens isolated over a period of several days or weeks after transduction, either from sacrificed animal models or biopsies. LacZ analysis of monolayer cultures and epithelial tissues developed from primary keratinocytes grown on a collagen support as raft cultures are both well established LacZ expression techniques. (S. C. Dollard, et al. *Genes and Dev.* 1992, 6:1131–1142; & J. L. Wilson et al., *Cell Growth Diff.* 1992, 3:471–483). Parker et al., *Cell Growth Diff.* 1997, 8:751–762, Zhao et al., *J. Virol.* 1997, 71:8832–8840. Similarly, nuclear directed β-galactosids readily detected in rodent airways in vivo after lipid mediated gene transfer, as well as in murine tracheal explants from animal models using recombinant adenoviral vectors. In addition, LacZ expression is detectable using a quantitative β-galactosidase activity assay (Galactolyte; Tropix, Inc.) using a fluorescent substrate for β-galactosidase. The control in such analyses is a plasmid devoid of HPV sequences, so that it does not replicate, for example pCMV-LacZ which expresses the LacZ gene from the same promoter employed in the instant invention. The procedure used for β-galactosidase staining consists of washing cells twice with phosphate buffered saline (PBS), fixing the cells in 2% formaldehyde plus 0.2% glutaraldehyde in PBS for 10 minutes. The fixed cells are rewashed twice and then stained in 20 mM $MgCl_2$, 5 mM potassium ferrocyanide, and 40 mg/ml X-gal chromagen (5-bromo-4-chloro-2-indolyl-β-D-galactopyranoside) in PBS. The cells are incubated in staining solution at 37° C. for 2 to 4 hours prior to visualization.

Luciferase. The luciferase reporter is attractive as a sensitive and quantitative method for transgene expression in lung homogenates from mice, as shown in FIG. 6 for the three plasmid replicon system of the instant invention. The luciferase gene is cloned into replicons with demonstrated persistence and therapeutic copy number levels, replacing LacZ. The control in such analyses is preferably pGL3c, an SV40 promoter-driven luciferase gene.

Enhanced Green Fluorescence Protein. The EGFP gene is an attractive reporter in cultured cells as well as in vivo due to the ability to identify transduced cells spectroscopically with quantitive digital light microscopy. Detection of gene EGFP in airway tissues was reported by Dr. T. Flotte at the 1997 Cystic Fibrosis Foundation Meeting Williamsburg, Va., USA. Variants of GFP are now available and can substitute readily for one another as reporters in this assay.

EXAMPLE 17

DNA Delivery by Complexing with a Lipid (2) DNA in complex with GL-67. Lipid 67 (Genzyme Corp., Framingham, Mass.) is an efficient reagent for DNA delivery to mammalian lung and augments the transgene expression by 100–1,000-fold. Lee et al., *Human Gene Therapy* 1996, 7:1701–1707. The lipid transfers plasmid-based genes to murine and non-human primate airways at a level roughly equivalent to recombinant adenovirus at an multiplicity of infection (MOI) of 20. S. Cheng, as reported in the Nonviral Vectors Workshop, The North American CF Meeting, Orlando, Fla. 1996). For lipid/DNA instillation into mice, a total of 650 $\mu$g of plasmid is complexed with 108 $\mu$g of GL-67 in a final volume of 550 $\mu$l. The complex is allowed to form without stirring at 30° C. for 5 min prior to instillation into a mouse (100 $\mu$l/mouse). For "naked" DNA instillation, the same procedures will be followed in the absence of GL-67. In previous studies, it has been shown that administration of genes by this technique is equivalent in mouse lungs whether the material is instilled by a tracheal cut-down and intracatheter instillation, or simply instilled into the mouse nostril so that the animal "sniffs" the material into the lungs. Accordingly, one instills 100 $\mu$l aliquots of GL-67/plasmid replicon formulations to groups of six mice. Mice are sacrificed at time points (t=2 d, 4 d, 7 d, 14 d, 21 d or longer); lungs are snap-frozen in liquid $N_2$ and pulverized with mortar and pestle or Braun tissue homogenizer to a fine powder. The powder is processed for luciferase assay. This same approach demonstrates luciferase signals, even with low level luciferase-expressing plasmids in the lung (for example, an SV40-driven plasmid containing luciferase, pGL3c). For measurements of replicon persistence or replication, lung tissues removed at the same time points described above are subjected to an alkaline Hirt extraction protocol such as in FIG. 5. After RNase treatment, the low molecular weight DNA is Southern blotted or PCR amplified with appropriate primer pairs after appropriate restriction enzyme digestion together with Dpn I as described in Example 7. PCR-positive results following Dpn I digestion indicate persistent input DNA and plasmid replication in the mouse airways.

EXAMPLE 18

Determination of Optimum Levels of HPV Replication in vivo for a Preselected Transgene A successful therapeutic transduction requires that the host immune system does not eliminate those cells in which a replicon has been successfully established and a transgene efficiently expressed. Prior to therapeutic administration, replicon persistence and expression are optionally contrasted between immune-compromised and immune-competent animal models. Immune compromised models include severe combined immunodeficiency (SCID) mice. Optimal levels of HPV replication proteins (as reflected by replicon copy number in vitro) and the possible effects of E4 and E5 proteins on plasmid persistence in vivo result. Reporter gene expression (LacZ or luciferase), and plasmid persistence are assayed over a period of several days or weeks as per the method of Example 17 for mice tissue.

If the persistence results in SCID mice are consistently better than results in immune-competent mice, according to these assays, then the host immune system is imposing deleterious restriction on reporter expression and replicon persistence. For instance, if a replicon without a reporter only persists in SCID mice, then the levels of E1 and E2 proteins are likely too high and replicons with lower copy numbers are evaluated as part of the in vivo development. If a replicon without a reporter persists in both immune-competent and immune-comprised mice, then the levels of E1 and E2 proteins are likely not a problem in therapeutic administration. If the same replicon except for a reporter has more extended persistence in SCID mice relative to immune-competent mice, the target of immune reactions is likely to be the reporter gene product, and is tested by using a weaker promoter, such as the URR itself, to express the reporter gene, as per Example 15.

Any publications mentioned in this specification are indicative of the levels of skill in the art relevant to the instant invention. These publications are incorporated herein by reference.

EXAMPLE 19

Adenovirus VAI and VAII Genes

The VA genes are included in most of the preceding example replicons. The presence of these genes enhances the translation of E1 and E2 proteins from messages that contain the 5' untranslated adenovirus tripartite leader. Replicons devoid of these genes have a reduced replication efficiency in transient replication assays. One may determine whether the genes also modulate translation when a host cell promoter such as that for PCNA or DNA polymerase $\alpha$ is used in the absence of the 5' untranslated adenovirus tripartite leader sequences. VA genes are optionally deleted if the transgene is an antisense RNA or ribozyme, which are not intended for translation.

Any publications mentioned in this specification are indicative of the levels of skill in the art relevant to the instant invention. These publications are incorporated herein by reference.

Various modifications of the instant invention in addition to those shown and described herein will be apparent to those skilled in the art from the above descriptions. Such modifications are also fully intended to fall within the scope of the appended claims.

What is claimed is:

1. A replicon for delivery of a transgene for episomal gene expression in a mammalian host cell comprising:
    a transgene having an open reading frame or other nucleic acid sequence for transcription into RNA and under the transcriptional control of a first surrogate promoter and an expression enhancer sequence wherein said first surrogate promoter is selected from a group consisting of: HPV-6, HPV-11, HPV-16, HPV-18 and wherein said expression enhancer sequence is selected from a group consisting of: HPV-6 upstream regulatory region, HPV-11 upstream regulatory region, HPV-16 upstream regulatory region, HPV-18 upstream regulatory region an endogenous HPV upstream regulatory region;
    a first gene sequence expressing the HPV viral replication initiator protein E1 under the control of an endogenous HPV upstream regulatory region; and a second gene sequence expressing the HPV viral replication origin-binding protein E2 under the control of an endogenous HPV upstream regulatory region, wherein said transgene, said first and said second sequences are incorporated within at least one plasmid and less than three plasmids.

2. The replicon of claim 1 wherein said first surrogate promoter and said expression enhancer sequence are of the same origin.

3. The replicon of claim 1 wherein said expression enhancer sequence is an HPV-11 upstream regulatory region.

4. The replicon of claim 1, wherein said transgene is a cystic fibrosis transmembrane regulator.

5. The replicon of claim 1 wherein said transgene is a reporter gene selected to measure replicon transfection and replication efficiencies.

6. The replicon of claim 1 wherein said transgene is selected from a group consisting of: luciferase, LacZ, EGFP, blue fluorescent protein, and other reporter genes.

* * * * *